United States Patent
Ando et al.

(10) Patent No.: US 9,301,881 B2
(45) Date of Patent: Apr. 5, 2016

(54) WEARING ARTICLE AND METHOD OF MANUFACTURING SAME

(75) Inventors: Kenji Ando, Tochigi (JP); Yasuhiro Umeki, Tochigi (JP); Toshiaki Ichimata, Tochigi (JP)

(73) Assignee: KAO CORPORATION, Tokyo (JP)

( * ) Notice: Subject to any disclaimer, the term of this patent is extended or adjusted under 35 U.S.C. 154(b) by 742 days.

(21) Appl. No.: 13/140,859

(22) PCT Filed: Dec. 24, 2009

(86) PCT No.: PCT/JP2009/071409
§ 371 (c)(1),
(2), (4) Date: Jun. 22, 2011

(87) PCT Pub. No.: WO2010/074131
PCT Pub. Date: Jul. 1, 2010

(65) Prior Publication Data
US 2011/0251576 A1    Oct. 13, 2011

(30) Foreign Application Priority Data

Dec. 24, 2008 (JP) ................ 2008-326784
Sep. 15, 2009 (JP) ................ 2009-213737

(51) Int. Cl.
*A61F 13/49*    (2006.01)
*A61F 13/15*    (2006.01)

(52) U.S. Cl.
CPC ..... *A61F 13/15593* (2013.01); *A61F 13/49011* (2013.01)

(58) Field of Classification Search
CPC .............. A61F 13/15593; A61F 13/49011; A61F 13/4902; A61F 13/49061
See application file for complete search history.

(56) References Cited

U.S. PATENT DOCUMENTS

| 4,834,741 A | 5/1989 | Sabee |
| 5,167,897 A | 12/1992 | Weber et al. |

(Continued)

FOREIGN PATENT DOCUMENTS

| CN | 1069648 A | 3/1993 |
| CN | 1078379 A | 11/1993 |

(Continued)

OTHER PUBLICATIONS

International Preliminary Report on Patentability and Written Opinion of the International Searching Authority (Forms PCT/IB/338, PCT/IB/373 and PCT/ISA/237), dated Aug. 18, 2011, for Application No. PCT/JP2009/071409.

(Continued)

*Primary Examiner* — Susan Su
(74) *Attorney, Agent, or Firm* — Birch, Stewart, Kolasch & Birch, LLP

(57) ABSTRACT

A wearing article (1) of the invention has edge sections (leg edge sections and waist edge section) configured including sheets. On the sheets in the edge sections, elastic members (6, 7, 8) are disposed in their stretched state along the edge sections. Draw-processed sections (P1, P2) are formed by performing draw processing, in the stretching direction of the elastic members (6, 7, 8), on the disposition sections of the sheets where the elastic members (6, 7, 8) have been disposed. Furthermore, a draw-processed section (P3) is formed by performing draw processing, in the stretching direction of an elastic member (5), on the disposition section of a band-shaped sheet (15), which configures three-dimensional gathers (18), where the elastic member (5) has been disposed.

14 Claims, 9 Drawing Sheets

(56) References Cited

U.S. PATENT DOCUMENTS

| | | | |
|---|---|---|---|
| 5,236,430 A | 8/1993 | Bridges | |
| 5,242,436 A | 9/1993 | Weil et al. | |
| 5,843,068 A * | 12/1998 | Allen | A61F 13/49015 604/385.22 |
| 6,248,097 B1 * | 6/2001 | Beitz | A61F 13/15593 604/358 |
| 6,291,039 B1 * | 9/2001 | Combe | A41D 27/245 156/164 |
| 6,417,121 B1 * | 7/2002 | Newkirk | A61F 13/51401 428/198 |
| 7,368,027 B2 | 5/2008 | Schneider et al. | |
| 8,012,388 B2 * | 9/2011 | Akaki | B29C 55/18 264/288.4 |
| 2001/0034508 A1 * | 10/2001 | Betrabet | A61F 13/15699 604/358 |
| 2001/0049516 A1 * | 12/2001 | Shimada | A61F 13/49011 604/385.11 |
| 2002/0010450 A1 * | 1/2002 | Suzuki | A61F 13/496 604/385.01 |
| 2002/0022818 A1 * | 2/2002 | Mishima | A61F 13/49015 604/385.29 |
| 2002/0026171 A1 * | 2/2002 | Sayama | A61F 13/49011 604/385.3 |
| 2002/0040215 A1 * | 4/2002 | Suzuki | A61F 13/49473 604/385.28 |
| 2002/0193774 A1 * | 12/2002 | Otsubo | A61F 13/51464 604/385.22 |
| 2003/0088226 A1 * | 5/2003 | Takagi | A61F 13/15593 604/385.16 |
| 2004/0006323 A1 * | 1/2004 | Hall | A61F 13/15593 604/385.24 |
| 2004/0127865 A1 * | 7/2004 | Mitsui | A61F 13/539 604/358 |
| 2004/0236299 A1 * | 11/2004 | Tsang | A61F 13/15756 604/385.24 |
| 2005/0065491 A1 | 3/2005 | Schneider et al. | |
| 2006/0035055 A1 * | 2/2006 | Schneider | A61F 13/4902 428/105 |
| 2006/0111686 A1 * | 5/2006 | Schneider | A61F 13/49011 604/385.26 |
| 2007/0167929 A1 * | 7/2007 | Fossum | A61F 13/4902 604/385.3 |
| 2008/0215025 A1 | 9/2008 | Schneider et al. | |
| 2009/0035527 A1 * | 2/2009 | Kobayashi | A61F 13/15593 428/167 |
| 2009/0326504 A1 * | 12/2009 | Kaneda | 604/385.23 |
| 2010/0022151 A1 | 1/2010 | Malowaniec | |
| 2010/0234823 A1 * | 9/2010 | Morita | A61F 13/4902 604/385.22 |
| 2010/0312207 A1 * | 12/2010 | Rezai | A61F 13/5622 604/365 |
| 2011/0066127 A1 * | 3/2011 | Kuwano | A61F 13/49001 604/385.3 |
| 2011/0118689 A1 * | 5/2011 | Een et al. | 604/385.3 |
| 2014/0236114 A1 * | 8/2014 | Goodlander | A61F 13/4902 604/385.29 |
| 2015/0051569 A1 * | 2/2015 | Hashimoto | A61F 13/496 604/385.16 |

FOREIGN PATENT DOCUMENTS

| | | |
|---|---|---|
| DE | 102007018377 A1 | 10/2008 |
| EP | 2022453 A1 | 2/2009 |
| JP | 7-501246 A | 2/1995 |
| JP | 2003-73967 A | 3/2003 |
| JP | 2005-27839 A | 2/2005 |
| JP | 2006-27089 A | 2/2006 |
| JP | 2007-503940 A | 3/2007 |
| JP | 2008-30468 A | 2/2008 |
| JP | 2008-36198 A | 2/2008 |
| JP | 2008-61693 A | 3/2008 |
| JP | 2008-137271 A | 6/2008 |
| JP | 2008-161572 A | 7/2008 |

OTHER PUBLICATIONS

International Search Report, dated Feb. 2, 2010, issued in PCT/JP2009/071409.

* cited by examiner

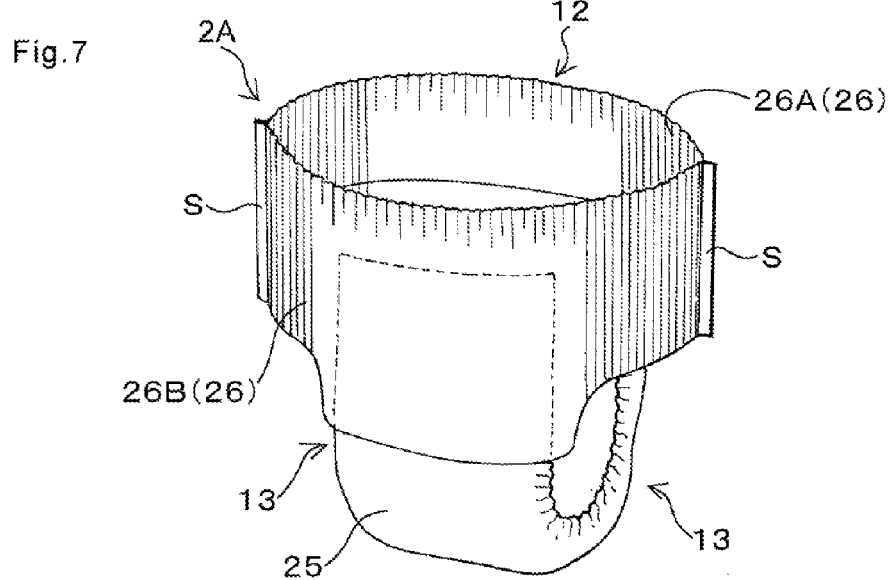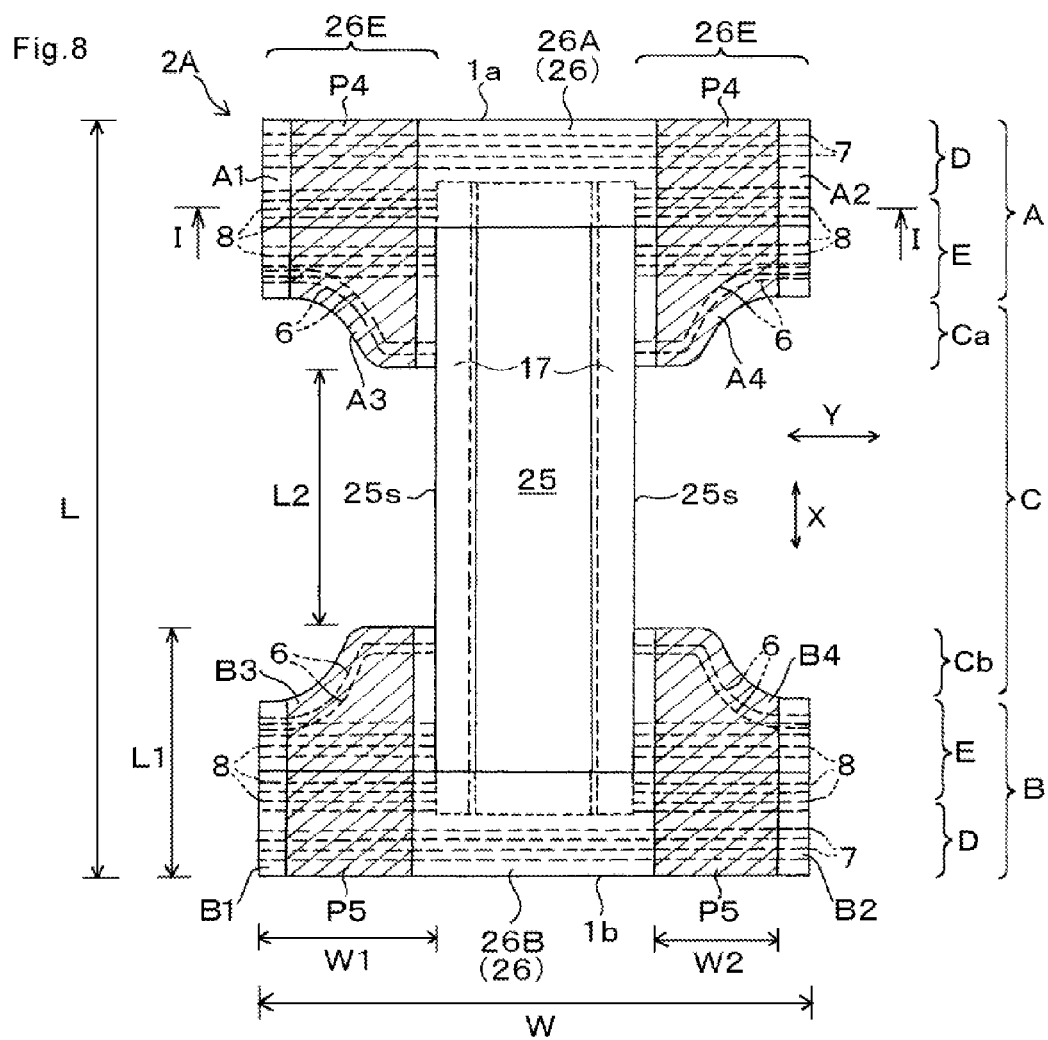

WEARING ARTICLE AND METHOD OF MANUFACTURING SAME

TECHNICAL FIELD

The present invention relates to a wearing article such as a disposable diaper, a sanitary napkin, or a disposable undergarment, and a method of manufacturing the same.

BACKGROUND ART

Among disposable diapers, which are one type of wearing article, there are known to be expandable-type disposable diapers that have fastening tapes and pull-on disposable diapers that are pre-formed into an underpants shape. Both of these types of diapers have a waist opening through which the torso of the wearer is inserted during wearing and leg openings through which the legs of the wearer are inserted. These openings are usually formed by connecting the edge sections of the diaper into a loop. These edge sections are usually configured including a sheet such as a nonwoven fabric. Also, both of these types of diapers have a back-side section arranged on the back side of the wearer during wearing and a stomach-side section arranged on the stomach side. The back-side section and stomach-side section of the diapers are normally configured including a sheet such as a nonwoven fabric.

There are cases where the peripheral edge sections of the waist opening and the leg opening, or the back-side section and the stomach-side section, of a disposable diaper separate from the body of the diaper wearer and become loose or slide down due to the wearer's movement or the like. In order to prevent such an inconvenience, the openings' peripheral edge sections, for example, the peripheral edge section of the waist opening (the waist edge section) in the back-side section and the stomach-side section, are provided with elastic stretchability. Another known technique for a disposable diaper provided with an absorbent body including an absorbent core and a sheet-shaped exterior body joined to the skin-non-contacting side of the absorbent body is to provide the exterior body constituting the back-side section and the stomach-side section with elastic stretchability for the purpose of improving the fit of the diaper to the wearer. In general, in the case of providing a disposable diaper with elastic stretchability, a method is generally used in which string-shaped or band-shaped elastic members in their stretched state are fixed between two substantially non-stretchable sheets via an adhesive, and gathers are formed by allowing the elastic members to shrink.

Also, as a material used in the wearing article, Patent Literature 1, for example, discloses a conjugate stretchable material in which two sheets and an elastic member are intermittently joined in the stretching direction of the elastic member, joints between one of the sheets and the elastic member are provided between joints between the other sheet and the elastic member in the stretching direction, and in each of the sheets, raised protrusion sections are formed between the joints. The conjugate stretchable material disclosed in Patent Literature 1 has many creases that extend in the direction intersecting with the stretching direction of the elastic member, resulting in the formation of a fiber structure having coarseness and fineness at the surface, thus realizing a soft and favorable feel against one's skin. Patent Literature 2 discloses a method of obtaining a nonwoven fabric having superior flexibility by subjecting a thermoplastic polymer nonwoven fabric to gear drawing under a predetermined draw ratio condition.

Patent Literature 3 discloses a method of manufacturing a disposable diaper including a drawing step in which a band-shaped sheet whose stretchability can be increased by drawing is fed between a pair of toothed rollers having teeth and grooves meshed with each other and is drawn in the width direction, thus increasing the widthwise stretchability of the band-shaped sheet. Also, Patent Literature 4 discloses a method of manufacturing a disposable diaper including a step in which a zero-strain stretch laminate web is supplied between pressure applicators having three-dimensional surfaces that are meshed with each other, and elasticity is provided by drawing part of the web through the application of pressure by the applicators. In the methods for manufacturing a disposable diaper disclosed in Patent Literature 3 and 4, an elastic member that forms various types of gathers is fixed between two pre-drawn sheets via an adhesive; that is, the sheets are subjected to draw processing before the elastic member is fixed to the sheets.

CITATION LIST

Patent Literature

Patent Literature 1: JP-A-2006-27089
Patent Literature 2: JP-A-2003-73967
Patent Literature 3: JP-A-2008-61693
Patent Literature 4: U.S. Pat. No. 5,167,897A

SUMMARY OF INVENTION

Technical Problem

Incidentally, in conventional disposable diapers, gathers are normally formed in the edge sections of the diaper, including the edge sections of the waist opening and the leg openings, or the back-side section and the stomach-side section constituted by the exterior body or the like, from the standpoint of texture, leakage prevention, and the like. These gathers, however, are formed by substantially inextensible sheets such as nonwoven fabric or resin sheets. For this reason, the edge sections hardly stretch even if pulled along the length direction, and if the disposable diaper is forcibly pulled on, the wearer will feel discomfort due to the edge sections constricting the wearer's body. The edge sections will rupture if they are pulled even more forcibly. Also, the back-side section and the stomach-side section hardly stretch even if pulled along the hip direction of the wearer, and if the disposable diaper is forcibly pulled on, the wearer will feel discomfort due to the waist edge section and the like constricting the wearer's body. The waist edge section will rupture if the back-side section and the stomach-side section are pulled even more forcibly. In this way, with conventional disposable diapers whose edge sections or back-side section and stomach-side section are substantially inextensible, there is little change in the external shape and dimensions, thus having problems such as the worn diaper hindering the wearer's movement and tightly constricting the wearer's body. Also, there is a narrow range of size application, and there has not been sufficient accommodation for the various physical characteristics and body shapes of wearers. For this reason, it has been necessary to provide various types of diapers (an entire size lineup) with slightly different external shapes and dimensions in order to accommodate the various physical characteristics and body types of diaper wearers, thus leading to the disadvantage of, for example, soaring manufacturing costs due to the heavy usage of material.

The present invention therefore relates to providing a wearing article with a wide range of size application and a method of manufacturing the same.

Solution to Problem

The present invention relates to a wearing article including a section in which an elastic member has been disposed, in its stretched state, on a sheet, wherein a disposition section of the sheet where the elastic member has been disposed is provided with extensibility by subjecting the disposition section to draw processing in a stretching direction of the elastic member.

Also, the present invention (first invention) relates to providing a wearing article, wherein: the wearing article has an edge section configured including the sheet; on the sheet in the edge section, the elastic member is disposed in its stretched state along the edge section; and the disposition section of the sheet where the elastic member has been disposed is subjected to draw processing in the stretching direction of the elastic member.

The present invention also relates to providing a method of manufacturing the wearing article of the first invention, the method including: preparing a conjugate sheet by joining an elastic member, in its stretched state, to an edge section of a sheet along the edge section; and performing draw processing on a section of the conjugate sheet where the elastic member has been disposed by feeding the section between a pair of clamp bodies having teeth and grooves meshed with each other, the section being fed with the conjugate sheet stretched in a stretching direction of the elastic member.

Also, the present invention (second invention) relates to providing a wearing article, wherein: the wearing article has a back-side section to be arranged on a back side of a wearer and a stomach-side section to be arranged on a stomach side of the wearer, the back-side section and the stomach-side section each being configured including the sheet; on the sheet in the back-side section and/or the stomach-side section, the elastic member is disposed in its stretched state along a hip direction of the wearer; and a draw-processed section is formed in the back-side section and/or the stomach-side section, the draw-processed section including the elastic member and being made by providing the sheet itself with extensibility by draw processing.

The present invention also relates to providing a method of manufacturing the wearing article of the second invention, the method including: preparing a conjugate sheet by joining an elastic member, in its stretched state, to a sheet configuring a back-side section or a stomach-side section of the wearing article, the elastic member being joined along a hip direction of a wearer; and performing draw processing on a predetermined section of the back-side section or the stomach-side section in the conjugate sheet by feeding the predetermined section between a pair of clamp bodies having teeth and grooves meshed with each other, the predetermined section being fed with the conjugate sheet stretched in a stretching direction of the elastic member.

Advantageous Effects of Invention

According to the present invention, it is possible to provide a wearing article with a wide range of size application in which the range of size application can be widened even if the amount of material is small, with which it is possible to accommodate various physical characteristics and body types of wearers, and in which a reduction in manufacturing cost has been achieved. Also, the present invention enables the production of a wearing article that, even if the wearing article is manufactured using pattern paper of a predetermined size, can accommodate a size outside the range normally assumed for that size of pattern paper, and thus it is possible to provide a wearing article with a large size even if the amount of material is relatively small. Since the amount of material used can be reduced, the amount of resources used is small, thus achieving environmental-friendliness. Also, according to the present invention, it is possible to form gathers having regularly aligned creases. Also, with the wearing article provided by the present invention (first invention), the edge sections that encircle portions of the wearer's body gently come into contact with the skin, thus achieving leeway with little constriction, a low likelihood of leaving an impression of the edge section on the skin, and superior wearing comfort. Also, with the wearing article provided by the present invention (second invention), the back-side section and the stomach-side section gently come into contact with the skin, thus achieving leeway with little constriction, a low likelihood of leaving an impression of edge sections such as the waist edge section on the skin, and superior wearing comfort.

BRIEF DESCRIPTION OF DRAWINGS

FIG. 7 is a perspective view showing a pull-on disposable diaper according to a first embodiment of the wearing article of the present invention (second invention).

FIG. 8 is a plan view of a skin-contacting side (topsheet side) schematically showing the disposable diaper shown in FIG. 7 in an expanded state in which the diaper has been spread out flat by stretching the elastic members in each section.

DESCRIPTION OF EMBODIMENTS

Figure 1:
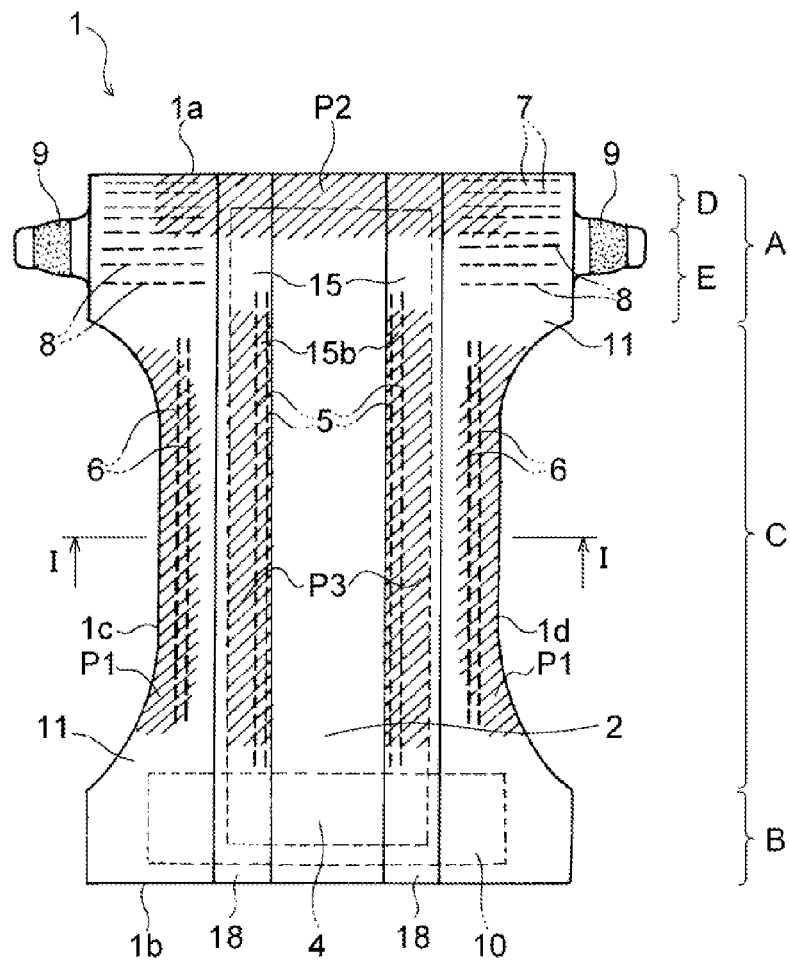
FIG. 1 is a plan view of a skin-contacting side (topsheet side) schematically showing a disposable diaper according to an embodiment of a wearing article of the present invention (first invention) in an expanded state in which the diaper has been spread out flat by stretching the elastic members in each section.
Figure 2:
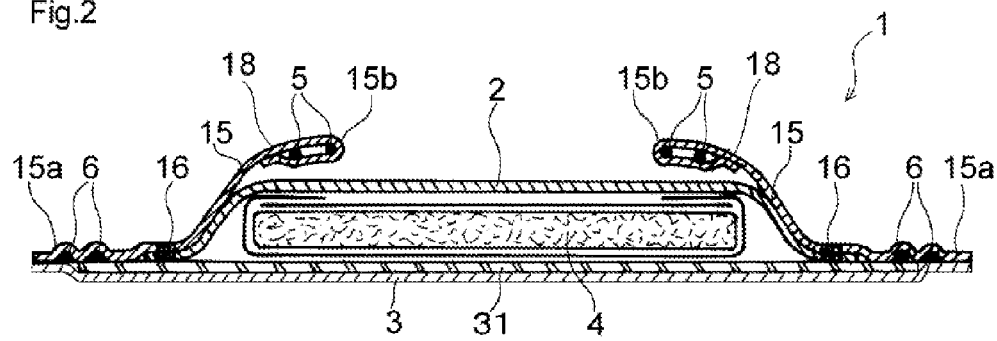
FIG. 2 is a cross-sectional view schematically showing a cross-section taken along line I-I in FIG. 1.

The following describes the present invention (first invention) based on preferred embodiments thereof with reference to the drawings. FIG. 1 is a plan view of a skin-contacting side (topsheet side) schematically showing a disposable diaper according to an embodiment of a wearing article of the present invention (first invention) in an expanded state in which the diaper has been spread out flat by stretching the elastic members in each section, and FIG. 2 is a cross-sectional view schematically showing a cross-section taken along line I-I in FIG. 1. A diaper 1 of the present embodiment is a wearing article having a waist edge section and leg edge sections as edge sections configured including a sheet. Note that in the present description, "edge section" refers to an area that includes the edge (end) of the article and the vicinity thereof and has a predetermined width along the edge.

As shown in FIGS. 1 and 2, the diaper 1 of the present embodiment is provided with a topsheet 2 forming a skin-contacting face, a backsheet 3 forming a skin-non-contacting face, and a liquid-retentive absorbent core 4 disposed between the two sheets 2 and 3, and is an expandable-type of diaper that has fastening tape 9 for fastening and has been formed so as to be substantially elongated. The diaper 1 has a back-side section A, a stomach-side section B, and a crotch section C located therebetween along the length direction. The back-side section A is at a site located on the back side of the wearer, the stomach-side section B is at a site located on the stomach side of the wearer, and the crotch section C is at a site located at the crotch of the wearer. The crotch section C is located in a lengthwise central section of the diaper 1. Note that in the present description, the skin-contacting face is the face of the wearing article and its constituent elements that faces the wearer's skin when the diaper is worn, and the skin-non-contacting face is the face of the wearing article and its constituent elements that faces away from the wearer's skin when the diaper is worn.

Opposite edges along the length direction of the crotch section C of the diaper 1 are curved into an inward-facing arc, and overall, the diaper 1 has an hourglass shape in which the lengthwise central section is narrow. The topsheet 2 has a substantially rectangular shape whose outer dimensions are larger than those of the absorbent core 4 as seen from above, and is arranged on the widthwise central portion of the backsheet 3. The backsheet 3 is made up of nonwoven fabric and the external shape thereof is an hourglass shape matching the external shape of the diaper. The topsheet 2 and the backsheet 3 extend outward from the opposite lengthwise edge sections and the opposite widthwise edge sections of the absorbent core 4, and are joined to each other in the extending sections thereof either directly, or via another member, with use of a joining means such as sealing or an adhesive. Also, a liquid-impermeable back-side inner-layer sheet 31 is arranged between the backsheet 3 and the absorbent core 4. The back-side inner-layer sheet 31 has a rectangular shape large enough to cover the entirety of the skin-non-contacting face of the absorbent core 4, has substantially the same width as the backsheet 3 in the crotch section C, and has a narrower width than the backsheet 3 in the back-side section A and the stomach-side section B. Also, although the lengthwise length of the back-side inner-layer sheet 31 is the same as that of the backsheet 3 in the present embodiment, the lengthwise length of the back-side inner-layer sheet 31 may be shorter than that of the backsheet 3 as long it can cover substantially the entirety of the skin-non-contacting face of the absorbent core 4.

The diaper 1 is provided with three-dimensional gathers 18, one edge section side of which is fixed to a face of the sheet forming the diaper 1 and the other edge section side of which can rise above that face with the fixed end serving as the rising base end. Specifically, paired three-dimensional gathers 18 that extend in the length direction of the diaper 1 are arranged at each lengthwise side section of the diaper 1. Each of the three-dimensional gathers 18 is provided with a band-shaped sheet 15 whose edge section 15a on one side in the width direction orthogonal to the length direction of the diaper 1 is fixed, and one or a plurality of (in the present embodiment, two) elastic members 5 for three-dimensional gather formation fixed in a stretched state at the other edge section (free-end edge section) 15b in the width direction of the band-shaped sheet 15 or the vicinity thereof. The elastic member 5 is disposed from the back-side section A to the stomach-side section B along the length direction of the diaper 1. Preferably, at least one elastic member 5 is arranged at a site within 60 mm, or more preferably 0 mm to 30 mm, from the edge on the other side (free-end edge) of the band-shaped sheet 15. The edge section 15a on the one side (fixed edge section) of the band-shaped sheet 15 is joined to the topsheet 2 along the length direction of the diaper 1 at a location outward of the opposite lengthwise side edges of the absorbent core 4, and a joint 16 thereof serves as a rising base end section 16 of the three-dimensional gather 18. The band-shaped sheet 15 extends outward from the rising base end section 16 in the width direction of the diaper 1, and is joined to the backsheet 3 in the extending section. The band-shaped sheet 15 is also joined onto the topsheet 2 in front and rear end sections in the length direction of the diaper 1.

Also, one or a plurality of (in the present embodiment, two) leg elastic members 6 are arranged substantially linearly at leg edge sections which are located at opposite lengthwise sides of the diaper 1 (i.e., side edge sections along the length direction of the diaper 1 in the crotch section C (side edge sections curved in an inward-facing arc)) or the vicinity thereof. The leg elastic members 6 are fixed by being clamped in their stretched state between the band-shaped sheet 15 and the backsheet 3 or the back-side inner-layer sheet 31 outward, in the width direction, of the elastic members 5 for three-dimensional gather formation. Thus, leg gathers are formed. The elastic member 6 is disposed from the back-side section A to the stomach-side section B along the length direction of the diaper 1. Preferably, at least one elastic member 6 is arranged at a site within 100 mm, or more preferably 0 mm to 50 mm, from lateral edges 1c and 1d of the diaper 1 (i.e., from peripheral edges of the leg openings of the diaper 1 in the worn state).

Also, waist elastic members 7 are disposed in the waist section D (waist edge section) in the back-side section A, thus forming waist gathers. The waist elastic members 7 are fixed by being clamped in their stretched state between the topsheet 2 and the backsheet 3 or the back-side inner-layer sheet 31 over substantially the entire width along the width direction of the diaper 1. Preferably, at least one elastic member 7 is arranged at a site within 80 mm, or more preferably 0 mm to 40 mm, from a lengthwise end edge 1a of the diaper 1 (i.e., from the peripheral edge of the waist opening of the diaper 1 in the worn state). The waist section D is an area that is at a site located around the wearer's waist, and normally has a length that is 1% to 15% of the total lengthwise length of the diaper 1 from the lengthwise end edge 1a of the diaper 1 in the back-side section A (or a lengthwise end edge 1b of the diaper 1 in the stomach-side section B).

Also, a plurality of elastic members 8 for hip gather formation are disposed at the opposite lengthwise side sections of a hip section E (in the vicinity of the waist edge section) in the back-side section A, thus forming a pair of left and right hip gathers. The elastic members 8 for hip gather formation are arranged substantially linearly along the width direction, and are fixed by being clamped in their stretched state between the topsheet 2 and the backsheet 3 or the back-side inner-layer sheet 31. The hip section E in the back-side section A is an area located below the waist section D and above the crotch section C when, as shown in FIG. 1, the diaper 1 is in a state of being spread out flat (expanded state) by stretching the elastic members of each section, considering the back-side section A side to be the top side and the stomach-side section B side to be the bottom side.

A pair of fastening tape pieces 9 are provided on the opposite lengthwise edge sections of the back-side section A. More specifically, side flaps 11 that extend laterally outward from the lateral edge sections of the absorbent core 4 are formed at the respective side sections of the back-side section A, and the fastening tape pieces 9 are attached to the side flaps 11 so as to extend laterally outward. A mechanical fastening hook member (not shown) is attached to each of the fastening tape pieces 9. Hook members known in the corresponding technical field can be used as the hook members without any particular limitation. Note that side flaps 11 that extend laterally outward are respectively formed on the opposite side sections of the stomach-side section B as well.

Also, landing tape pieces 10 for fastening of the fastening tape pieces 9 are affixed on the outer surface (skin-non-contacting face) of the stomach-side section B. The landing tape pieces 10 are configured by a rectangular base material sheet and a loop material attached to the base material sheet. The loop material is used as an engaging member that engages with the hook members attached to the fastening tape pieces 9.

As in an ordinary procedure, according to the diaper 1 of the present embodiment having the above-described configuration, the topsheet 2 side is abutted against the wearer's body, and the hook members of the pair of fastening tape pieces 9 located on the back side are fastened to the landing tape pieces 10 located on the stomach side, thereby forming a pair of leg openings (not shown) due to the lateral edges 1c and 1d of the diaper 1 and sites (leg edge sections) located in the crotch section C in the vicinity thereof all being connected to become annular, and forming a waist opening (not shown) due to the lengthwise end edges 1a and 1b of the diaper 1 and the vicinity thereof (waist edge sections) being connected to become annular.

Also, in the diaper 1 of the present embodiment, the elastic members 6 are disposed in a stretched state along the leg edge sections in the sheets in the leg edge sections (band-shaped sheet 15, back-side inner-layer sheet 31, and backsheet 3), and the disposition sections of the sheets, on which the elastic members 6 have been disposed, have been subjected to draw processing in the stretching direction of the elastic members 6 (length direction of the diaper 1), thus providing the disposition sections with extensibility. Also, the elastic members 7 and 8 are disposed in a stretched state along the waist edge sections in the sheets in the waist edge sections (topsheet 2, back-side inner-layer sheet 31, and backsheet 3), and the disposition sections of the sheets, on which the elastic members 7 and 8 have been disposed, have been subjected to draw processing in the stretching direction of the elastic members 7 and 8 (width direction of the diaper 1), thus providing the disposition sections with extensibility. In FIG. 1, the sites that have been subjected to draw processing (hereinafter, also referred to as "draw-processed sections") are diagonally hatched and denoted by reference signs P1 to P3 (reference sign P3 will be described later). Reference signs P1 indicate draw-processed sections in the leg edge sections (i.e., the peripheral edge sections of the leg openings), and reference sign P2 indicates a draw-processed section in the waist edge section (i.e., the peripheral edge section of the waist opening). Each draw-processed section P1 spans from the peripheral edge 1c or 1d of one of the leg openings to a position beyond the leg elastic member 6 located most inward in the width direction of the diaper. Also, in the back-side section A, the draw-processed section P2 spans from the opening peripheral edge 1a of the waist opening, beyond the waist section D, into part of the elastic members 8 in the hip section E.

Figure 3:
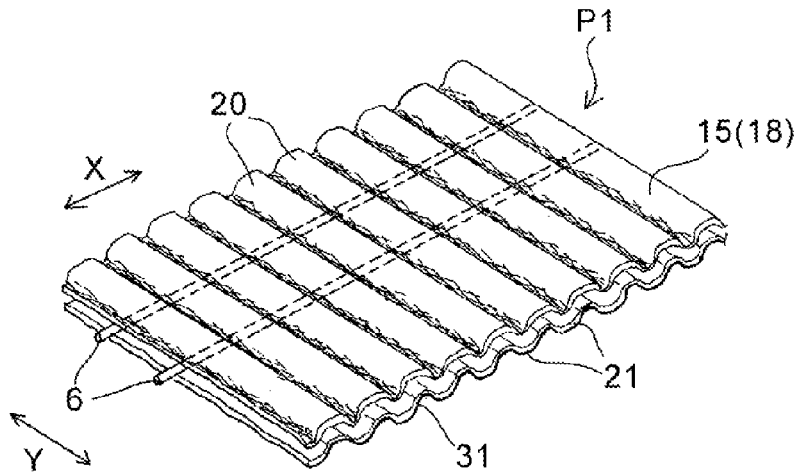
FIG. 3 is a perspective view schematically showing part of a leg edge section that has been subjected to draw processing (draw-processed section P1) in the disposable diaper in the expanded state shown in FIG. 1.

FIG. 3 schematically shows part of the draw-processed section P1 in the diaper 1 in the expanded state shown in FIG. 1. As shown in FIG. 3, in the draw-processed section P1, a multitude of ribbed creases 20 are formed by the band-shaped sheet 15 rising up convexly outward (toward the wearer's skin), and a multitude of ribbed creases 21 are formed by the back-side inner-layer sheet 31 rising up convexly outward (away from the wearer's skin). The multitude of creases 20 and 21 extend in a direction (the width direction of the diaper 1, which is the Y direction in FIG. 3) orthogonal to the stretching direction of the elastic members 6 (the length direction of the diaper 1, which is the X direction in FIG. 3), and the gathers are formed such that a multitude of these individual creases 20 and 21 are regularly lined up along the leg edge sections. As shown in FIG. 3, gathers are formed in the draw-processed section P2 and the later-described draw-processed sections P3 as well.

Due to the draw processing, in the sheets in the draw-processed sections P1 and P2, the sheets undergo plastic deformation due to part or all of the fibers or the like that are formation components of the sheets being stretched and/or fractured and thus broken down, without rupturing. Accordingly, the draw-processed sections readily stretch in the stretching direction of the elastic members and the amount of stretching is increased, compared with sites in the same sheet that have not been subjected to the draw processing (sites that have not been caused to plastically deform). In other words, the sheets themselves in the draw-processed sections P1 and P2 easily and readily stretch in the stretching direction of the elastic members even with low stress. For this reason, compared to the leg gather sections and waist gather sections in a conventional diaper that have not been subjected to draw processing, the draw-processed sections P1 and P2 stretch a greater amount when pulled in the stretching direction of the elastic members, and exhibit high extensibility, that is to say, readily stretch with a small amount of force. Also, in the draw-processed sections P1 and P2, since the elastic members are arranged in their stretched state, even if the sheets that readily stretch in the stretching direction of the elastic members are stretched in the stretching direction, the sheets do not remained stretched out due to the shrinking effect of the elastic members, and therefore shrunk gathers are easily formed as shown in FIG. 3.

The diaper 1 of the present embodiment has various types of superior effects because the draw-processed sections P1 and P2, which have increased extensibility in the stretching direction of the elastic members due to the draw processing, are included in leg edge sections arranged around the wearer's legs and the waist edge section arranged around the wearer's waist. Specifically, the diaper 1 of the present embodiment has a wider range of size application than that of a non-draw-processed product that has not been subjected to the draw processing, and therefore can accommodate various physical features and body types of wearers. Also, the leg edge sections (draw-processed sections P1) and the waist edge section (draw-processed section P2) gently come into contact with the wearer's skin, and therefore the diaper 1 has leeway with little constriction, a low likelihood of leaving an impression of edge sections on the skin, and superior wearing comfort. Also, an advantage of the diaper 1 of the present embodiment is that the diaper 1 can be obtained by merely stretching originally-provided members without changing the size of the diaper pattern paper (topsheet and backsheet) or adding new members, and therefore regardless of the fact that the diaper 1 has high performance, a cutback in material fees and a reduction in manufacturing cost can be achieved, and the diaper 1 is environmentally friendly. Also, in the leg edge sections and the waist edge section of the diaper 1, by subjecting the sheets constituting these sites to draw processing (a gear drawing method), gathers are formed such that a multitude of creases that extend in the direction orthogonal to the stretching direction of the elastic members are aligned along the edge sections as shown in FIG. 3, and such gathers that have regularly aligned creases improve the exterior (appearance) of the diaper 1.

Also, in the diaper 1 of the present embodiment, the disposition sections of the band-shaped sheet 15 forming the three-dimensional gathers 18, where the elastic members 5 for three-dimensional gather formation have been disposed (i.e., the other edge section sides (free edge sections) 15b of the three-dimensional gathers 18) have been subjected to draw processing in the stretching direction of the elastic members 5 (the length direction of the diaper 1). In FIG. 1, reference sign P3 denotes draw-processed sections in the three-dimensional gathers 18. Each draw-processed section P3 spans from the free-side edge of the band-shaped sheet 15 to a position beyond the elastic member 5 located most outward in the width direction of the diaper. Arranging the draw-processed sections at the free edge section at which three-dimensional gathers can rise up in this way is effective in widening the range of diaper size application, and is also effective in view of preventing leaks due to enabling the design of three-dimensional gathers that conform to the wearer's movements, and in view of enabling the formation of gathers that are regular in appearance.

The draw processing according to the present invention (first invention) is performed on part or all of the elastic member disposition sections in the sheets configuring the edge sections of the absorbent article, and furthermore, the draw processing is also performed on portions that are in the vicinity of the disposition sections and do not have the elastic members arranged therein. In other words, in the present invention, performing draw processing beyond the entirety of the elastic member disposition sections is not excluded. Accordingly, the draw-processed sections P1 to P3 are not limited to only the elastic member disposition sections in the sheets configuring the edge sections of the diaper 1, and they may include portions in which elastic members are not arranged. Also, letting T1 be the length of an edge on which a draw-processed section has been formed, and T2 be the length along the edge of the draw-processed section, the ratio of T2 to T1 (T2/T1) is preferably 0.1 to 10.0, or more preferably 0.2 to 0.9. Here, the edge on which the draw-processed section has been formed is the edge along which the draw-processed section lies. For example, in the case of the draw-processed section P1, this refers to the length along the leg opening edge of the draw-processed section P1, in the case of the draw-processed section P2, this refers to the length along the waist opening edge on the back-side section A side of the draw-processed section P2, and in the case of the draw-processed section P3, this refers to the edge (free-side edge) of the free edge section 15b of the band-shaped sheet 15 of the draw-processed section P3.

The sizes of the draw-processed sections P1 to P3 can be appropriately set according to, for example, the distance from the opening peripheral edge or the free-side edge at which three-dimensional gathers can rise up (hereinafter, also referred to as a "peripheral edge or the like") to the elastic member in the vicinity thereof. Preferably, the draw-processed sections P1 to P3 are formed from the peripheral edges or the like over a length that is 1% to 45%, or more preferably 1% to 10%, the total length in the direction orthogonal to the direction in which the peripheral edges or the like extend (e.g., in the case of the draw-processed sections P1 and P3, this refers to the total length in the width direction of the diaper 1, and in the case of the draw-processed section P2, this refers to the total length in the length direction of the diaper 1). The length of the draw-processed section P1 along the width direction of the diaper 1 is preferably 5 mm to 150 mm, or more preferably 5 mm to 50 mm, the length of the draw-processed section P2 along the length direction of the diaper 1 is preferably 0 mm to 150 mm, or more preferably 0 mm to 50 mm, and the length of the draw-processed section P3 along the width direction of the diaper 1 is preferably 0 mm to 150 mm, or more preferably 0 mm to 50 mm.

Also, although the stretch rate of the draw-processed sections P1 to P3 differs depending on, for example, the draw ratio realized by the draw processing and the material of the sheets subjected to draw processing (topsheet 2, back-side inner-layer sheet 31, backsheet 3, and band-shaped sheet 15), the stretch rate is preferably 2% to 500%, or more preferably 50% to 300%. Also, in this case, the stretch rate of a portion of the sheets not subjected to draw processing is 0% to 400%, and normally is smaller than the stretch rate of the draw-processed sections P1 to P3. Also, in the case where the sheets configuring the gathers in the draw-processed sections P1 to P3 are, for example, a later-described nonwoven fabric or resin sheet, the stretch rate of the gathers before draw processing is normally 2% to 400%.

The stretch rate is measured in the following way. For example, in the case of measuring the stretch rate of the draw-processed section P1, firstly a side flap of the diaper 1 is cut off, including the draw-processed section P1 in which the elastic members 6 are arranged in their stretched state. The side flap that was cut off is left in a loose state, and a pen or the like is used to make marks on the side flap in units of length (50 mm, 100 mm, 200 mm, or the like) in the stretching direction of the elastic members 6. The side flap is gripped on both sides outward of the marks, the side flap is stretched by being pulled in the stretching direction of the elastic members 6, and the dimension (marginal stretch length) between the marks is measured when the side flap can be stretched no farther. The marginal stretch length is divided by the length of the side flap before pulling (initial length), 1 is subtracted from the result, and the result of that is multiplied by 100, thus obtaining the stretch rate (%) of the draw-processed section P1. For example, if the initial length of the draw-processed section P1 is 50 mm, and the marginal stretch length is 75 mm, the stretch rate of the draw-processed section P1 is 50%.

In particular, the stretch rate of the draw-processed section P1 located in the peripheral edge section of the leg opening (leg edge section) is preferably 50% to 500%, or more preferably 100% to 300%, the stretch rate of the draw-processed section P2 located in the peripheral edge section of the waist opening (waist edge section) is preferably 10% to 150%, or more preferably 10% to 100%, and the stretch rate of the draw-processed section P3 located in the free edge section 15b of the band-shaped sheet is preferably 50% to 500%, or more preferably 100% to 300%.

The draw-processed sections P1 to P3 are obtained by subjecting the elastic member disposition sections of the sheets, as well as the elastic members, to draw processing, in a state where the sheets and the elastic members have been integrated by being joined while the elastic members are in their stretched state in the edge section of the sheets or in the vicinity thereof. The elastic members are put in their stretched state in this draw processing. The draw processing performed on sheets such as a nonwoven fabric or a resin sheet is performed using, for example, a gear drawing method of feeding the sheets through a pair of gears having teeth and grooves that are meshed with each other, as will be described later. The gears may be shaped as a pair of gear rollers whose teeth and grooves are meshed in a gear fashion (wavy rollers), or may be shaped as a flat plate or have a diagonal teeth shape. The draw processing can be performed using, for example, the gears disclosed in Patent Literature 1 described above (e.g., see the disclosure of FIGS. 3 and 5 in Patent Literature 1).

In describing the materials for forming the various sections in the diaper 1, preferably the topsheet 2, the back-side inner-layer sheet 31, the backsheet 3, and the band-shaped sheet 15 are all sheets subjected to draw processing, and are made up of sheets suited for draw processing. A sheet suited for draw processing is a sheet that readily stretches when subjected to draw processing, but can ensure the strength of the sheet itself. As such a sheet, it is preferable to use (1) a sheet that does not have extensibility before drawing processing (i.e., is inextensible) but exhibits extensibility or stretchability after draw processing, or (2) a sheet somewhat having extensibility (low extensibility) even before draw processing but has improved extensibility or stretchability after draw processing (gains high extensibility), and examples of which include a nonwoven fabric, a resin sheet, an elastomer material, or a sheet conjugate material including an elastomer.

In particular, a nonwoven fabric is preferably used as the topsheet 2, the backsheet 3, and the band-shaped sheet 15 in view of breathability and extensibility. In particular, a liquid-permeable nonwoven fabric that allows a liquid such as urine to permeate is preferably used as the topsheet 2, and pores are formed as necessary. Also, in particular, a liquid-impermeable, moisture-permeable nonwoven fabric or a water-repellent, moisture-permeable nonwoven fabric is preferably used as the backsheet 3 and the band-shaped sheet 15. Also, a liquid-impermeable resin sheet is preferably used as the back-side inner-layer sheet 31.

Examples of the nonwoven fabric include nonwoven fabrics manufactured by various methods, such as a spun-bonded nonwoven fabric made up of elastic fibers or inelastic fibers, a meltblown nonwoven fabric, an SMS nonwoven fabric in which a spun-bonded nonwoven fabric and a meltblown nonwoven fabric are combined, an air-through nonwoven fabric, a heated roll nonwoven fabric, a spunlace nonwoven fabric, an air-laid nonwoven fabric, and a resin-bond nonwoven fabric. These nonwoven fabrics need to have a certain extent of basis weight and strength in order to prevent rupturing, but on the other hand, preferably the basis weight is 5 g/m² to 50 g/m², or more preferably 8 g/m² to 30 g/m², in view of the fact that breathability is hindered if the basis weight is too high and the nonwoven fabric is too thick.

Examples of the material of the fibers constituting the nonwoven fabric include synthetic resins such as polyethylene, polypropylene, polyester, or acrylic. The fibers constituting the nonwoven fabric may have been subjected to hydrophilization or water-repellency processing, or may be, for example, a conjugate fiber having a so-called core-in-sheath structure that has a sheath material with thermal adhesiveness at the surface of the core material. Preferably, fibers that readily exhibit extensibility due to draw processing are used in the nonwoven fabric.

Examples of the resin sheet include a film-shaped sheet made up of polyethylene, polypropylene, polyester, polyurethane, or the like. The resin sheet may be formed. In view of softness and strength, the thickness of the resin sheet is preferably 5 µm to 100 µm, or more preferably 8 µm to 30 µm. In view of the same, the basis weight of the resin sheet is preferably 5 g/m² to 50 g/m², or more preferably 8 g/m² to 30 g/m².

Also, as the absorbent core 4, it is possible to use any product used as an absorbent core in a conventional disposable diaper without any particular limitation, and for example, it is possible to use a fiber aggregate made up of hydrophilic fibers such as lumber pulp, or such a fiber aggregate provided with grains of superabsorbent polymer. Such fiber aggregates may be covered by a water permeable sheet such as paper or a nonwoven fabric.

Also, as the various types of elastic members 5, 6, 7, and 8, it is possible to use a known material conventionally used in this type of diaper, without any particular limitations. Examples of elastic member materials include synthetic rubbers such as styrene-butadiene, butadiene, isoprene, or neoprene, a natural rubber, EVA, SIS (styrene-isoprene-styrene), SEBS (styrene-ethylene-butylene-styrene), SEPS (styrene-ethylene-propylene-styrene), elastic polyolefin, or polyurethane. Also, the form of the various types of elastic members 5, 6, 7, and 8 can be appropriately selected from among thread-like, band-like, ribbon-like, film-like, net-like, and so on, and in particular, a thread-like or ribbon-like elastic member is preferable in view of being low-cost, having superior adhesiveness, having superior stretching responsiveness, and the ease of stress design.

Also, examples of the adhesive used in joining the various types of sheets 2, 31, 3, and 15 to the various types of elastic members 5, 6, 7, and 8 include a styrene-based (SIS, SBS, SEBS) or a polyolefin-based hot-melt adhesive.

Next is a description of a method of manufacturing the wearing article of the present invention (first invention) with reference to the drawings, taking the example of a method of manufacturing the above-described disposable diaper 1. Note that in the later description of the manufacturing method of the present invention, constituent portions similar to those of the embodiment described above have been given the same reference signs, and descriptions therefore have been omitted. Descriptions in the embodiment described above are to be appropriately applied to constituent portions not particularly described below.

Figure 4:
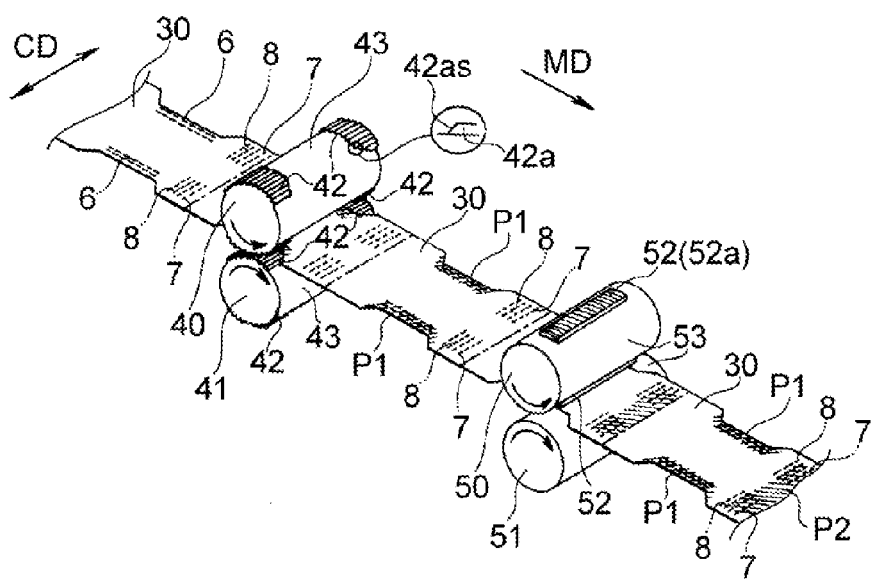
FIG. 4 is a schematic diagram showing a drawing step in the manufacturing of the disposable diaper shown in FIG. 1.

As shown in FIG. 4, the manufacturing method of the present embodiment has a step of preparing a continuous body of a diaper intermediate body 30 (conjugate sheet) by joining the elastic members 6, 7, and 8, in their stretched state, to and along the edge sections of laminate sheets, which were obtained by laminating three sheets (the topsheet 2, the back-side inner-layer sheet 31, and the backsheet 3), and performing draw processing on sections of the diaper intermediate body 30 where the elastic members 6, 7, and 8 have been disposed by feeding such sections between a pair of toothed rollers (clamp bodies) 40 and 41 that have teeth and grooves meshed with each other, the sections being fed with the diaper intermediate body 30 stretched in the stretching direction of the elastic members 6, 7, and 8. In the present embodiment, in addition to the pair of toothed rollers 40 and 41, another pair of toothed rollers 50 and 51 are also used as the clamps for performing draw processing.

The elastic members 6 are joined in their stretched state in the peripheral edge sections of the leg openings (leg edge sections) between the topsheet 2 and the back-side inner-layer sheet 31 or the backsheet 3, and the elastic members 7 and 8 are joined in their stretched state in the waist section D and the hip section E (waist edge section) on the back-side section A side, thus forming the diaper intermediate body 30. The diaper intermediate body 30 can be manufactured in a normal procedure using a method similar to the method of manufacturing this type of diaper. As shown in FIG. 4, the continuous body of the diaper intermediate body 30 is formed such that a plurality of diaper intermediate bodies 30 are connected so as to form a line in the length direction thereof. Note that when the elastic members are joined between the sheets 2, 31, and 3, joining may be achieved using an adhesive applied to the sheet side, but instead, a method of applying an adhesive to the elastic members in advance and adhering the elastic members to the sheets 2 and 31 is preferable in view of, for example, not impairing the flexibility of the sheet and not needing to align the adhesive application positions and the positions of the elastic members in manufacturing. Also, an adhesive may be applied to both the sheets and the elastic members with the object of improving the adhesiveness of the elastic members.

The paired toothed rollers 40 and 41 have teeth and grooves that extend in the roller axis direction (CD) on the circumferential face sections thereof, and that are meshed with each other. More specifically, as shown in FIG. 4, a pair of high stretch sections 42 provided with teeth and grooves is formed separated from each other in the roller axis direction on the circumferential face section of each of the paired toothed rollers 40 and 41, and a substantially flat low or non-stretching section 43 not provided with teeth and grooves is formed between the pair of high stretch sections 42 (in the central portion of the rollers in the roller axis direction). The pairs of high stretch sections 42 on the rollers 40 and 41 are formed so as to periodically mesh with each other as the rollers rotate. The object to be draw-processed (the diaper intermediate body 30) is subjected to draw processing in the direction MD between the pairs of high stretch sections 42.

Figure 5:
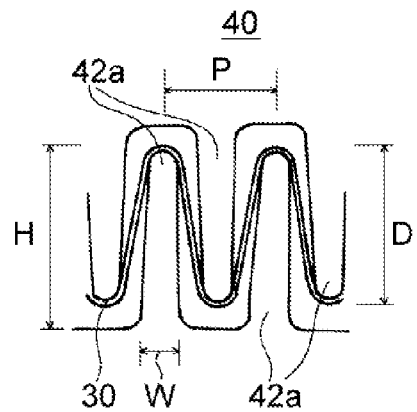
FIG. 5 is a schematic diagram showing how draw processing is performed on a conjugate sheet (diaper intermediate body) by toothed rollers in the drawing step shown in FIG. 4.

As shown in FIG. 5, teeth 42a having a predetermined height H are formed in each high stretch section 42, and when the high stretch sections 42 of the pairs of toothed rollers 40 and 41 mesh with each other, the teeth and grooves of the rollers mesh with each other to a predetermined mesh depth D. For this reason, in the object to be draw-processed (the diaper intermediate body 30), in the sheets in portions that have been fed between mutually opposing high stretch sections 42, part or all of the fibers that are the formation components of the sheets are stretched and/or broken, and the sheets plastically deform by being broken down to the extent that as a whole they do not rupture, thus obtaining high stretch areas that exhibit superior extensibility in the conveying direction (MD) of the object to be draw-processed.

As shown in FIG. 4, when viewed from the direction (MD) orthogonal to the roller axis direction, the teeth 42a that extend in the roller axis direction (CD) are formed as trapezoids with a width that decreases from the base of the teeth to the tips, and furthermore their side edges 42as located closer to the center in the roller axis direction are tilted. The tapered shape of the teeth 42a is a shape that provides the teeth 42a with necessary strength, as well as is a shape necessary for obtaining a high draw ratio. The end face of the teeth 42a has a smooth surface shape in order to do as little localized damage as possible to the sheet material and the elastic members during draw processing. Due to the teeth 42a having such a shape, when the object to be draw-processed is fed, it is possible to reduce the amount of localized damage done to the object to be draw-processed. Also, by subjecting the object to be draw-processed to the draw processing in gradation, it is possible to further reduce the damage done to the material. Gradation refers to gradually changing the draw ratio by, for example, giving the teeth a tapered shape as described above, in order to create a smooth boundary between the portions subjected to draw processing and the portions not subjected to draw processing, and reducing the change in the draw ratio between a draw-processed section at which the draw ratio exceeds 1× and a section that was not subjected to draw processing (section with a draw ratio of 1×).

On the other hand, the low or non-stretching sections 43 of the pair of toothed rollers 40 and 41 do not have teeth and grooves formed thereon and are substantially flat as described above, and therefore in the object to be draw-processed (the diaper intermediate body 30), the sheets in the portion that has passed through the mutually opposing low or non-stretching sections 43 substantially do not undergo plastic deformation, and become low or non-stretched areas that substantially do not exhibit extensibility. Note that in actual product processing, while conveying the product web, the portions not subjected to draw processing provide conveying tension, allowing processing at a constant tension. This enables processing while preventing phase shifting.

In order to raise the draw ratio of the object to be draw-processed and give the object to be draw-processed favorable extensibility, the mesh depth D (see FIG. 5) between the high stretch sections 42 of the pair of toothed rollers 40 and 41 is, although depending on the material of the object to be draw-processed, preferably 0.5 mm or more, or more preferably 0.5 mm to 5 mm. As shown in FIG. 5, the mesh depth D of the pair of toothed rollers 40 and 41 is the length for which adjacent teeth 42a overlap each other when the toothed rollers 40 and 41 are meshed together and rotated.

In the present embodiment, from the viewpoint of reliably achieving effects obtained by the above-described draw-processed sections P1 and P3 (sections that have been subjected to draw processing), the draw ratio achieved by the draw processing performed on the object to be draw-processed (diaper intermediate body 30) is preferably 1.02 times or more, or more preferably 1.1 times or more. In other words, the draw ratio (stretch ratio) of the sheets and elastic members in the portions where the high stretch sections 42 mesh with each other is preferably 1.02 times or more, or more preferably 1.1 times or more. Specifically, if the draw ratio is too high, there is the risk of leading to, for example, insufficient sheet strength due to the draw processing causing too much damage to the sheets, and therefore the maximum draw ratio is, although depending on the material used for the sheets, preferably approximately 5.0 times. Here, the draw ratio indicates how-many-fold the original sheets stretch according to the settings of the draw processing devices such as rollers having teeth and grooves, and therefore is defined as "material length after material has been drawn by meshing of rollers having teeth and grooves"/"material length before performing drawing by meshing of rollers". The draw ratio can be adjusted through the mesh depth of the teeth in the draw processing apparatus having teeth and grooves, the pitch of adjacent teeth, the width of the teeth, and the like.

Also, the pitch P of adjacent teeth (see FIG. 5) of the high stretch sections 42 of the toothed rollers 40 and 41 is preferably 0.5 mm to 20 mm, or more preferably 0.5 mm to 10 mm. Also, the width of the teeth 42a (length in the draw processing direction (MD)) W (largest width, see FIG. 5) is preferably less than ½ the pitch P, and furthermore the height H of the teeth 42a (see FIG. 5) is preferably 0.5 mm to 20 mm, or more preferably 0.5 mm to 10 mm. If the form of the teeth and grooves of the toothed rollers 40 and 41 satisfy such conditions, the object to be draw-processed (diaper intermediate body 30) that is fed between the toothed rollers 40 and 41 can be given high extensibility.

Note that the pitch of the teeth refers to the distance between the center line of one tooth and the center line of an adjacent tooth. The width of the teeth of the toothed rollers refers to the width of one tooth. The width W of the teeth 42a may be uniform across the tooth height direction, may be trapezoidal so as to decrease from the base of a tooth toward the tip, or may be rectangular, triangular, or the like. The height of the teeth of the rollers refers to the height from the base of a tooth to the tip.

In general, a gear defined in JIS B1701 is attached to the roller shafts of the toothed rollers 40 and 41 as a drive gear, separately from the teeth 42a. Then, by rotating due to the meshing of these drive gears, the rollers 40 and 41 rotate in synchronization without direct contact between the teeth 42a of the rollers 40 and 41.

Toothed rollers 50 and 51, constituting a pair, have teeth and grooves that extend in a direction (MD) orthogonal to the roller axis direction on the respective circumferential face sections thereof, and that are meshed with each other. More specifically, as shown in FIG. 4, a pair of high stretch sections 52 provided with teeth and grooves is formed separated from each other in the roller circumference direction on the circumferential face section of each of the paired toothed rollers 50 and 51, and a substantially flat low or non-stretching section 53 not provided with teeth and grooves is formed between the pair of high stretch sections 52 on each roller. The pairs of high stretch sections 52 on the rollers 50 and 51 are formed so as to periodically mesh with each other as the rollers rotate. Draw processing is performed on the object to be draw-processed (diaper intermediate body 30) in the CD direction between the pair of high stretch sections 52 and 52 of the toothed rollers 50 and 51, and therefore there is little reduction in strength in the MD direction due to the draw processing. For this reason, although a large portion in the width direction of the object to be draw-processed is subjected to draw processing between the toothed rollers 50 and 51, it is possible to sufficiently provide conveying tension.

Teeth 52a with a predetermined height are formed on the high stretch sections 52. The high stretch sections 52 are formed substantially the same as the high stretch sections 42 of the toothed rollers 40 and 41, with the exception that the teeth and grooves extend in the direction (MD) orthogonal to the roller axis direction. With the high stretch sections 52, gradation (taper) processing has been performed on the teeth shape in portions where the meshing begins and sections where the meshing ends. This gradation is as described above. The high stretch sections 52 can be formed, for example, as described in paragraph 0044 and FIG. 5 of the above-described Patent Literature 1.

In the object to be draw-processed (the diaper intermediate body 30), in the sheets in portions that have been fed between mutually opposing high stretch sections 52, part or all of the fibers that are the formation components of the sheets are stretched and broken, and the sheets plastically deform by being broken down to the extent that as a whole they do not rupture, thus obtaining high stretch areas that exhibit superior extensibility in the direction (CD) orthogonal to the conveying direction of the object to be draw-processed. On the other hand, in the object to be draw-processed (the diaper intermediate body 30), the sheets in portions that have been fed between mutually opposing low or non-stretching sections 53, substantially do not undergo plastic deformation, thus obtaining low or non-stretching areas that substantially do not exhibit extensibility.

The interval between the toothed rollers 40 and 41 and the interval between the toothed rollers 50 and 51, through which the object to be draw-processed passes, can both be appropriately set finely, and controlling the intervals enables easily changing the draw ratio of the object to be draw-processed. One of the toothed rollers in each pair is provided with an elevating function with use of a cylinder or the like (not shown), thus easily controlling the interval. Although not shown, a shim or the like can be used to finely adjust the intervals. Note that although the toothed rollers are configured such that the toothed portions and rollers are formed integrally as a single unit in the illustrated example, a configuration is possible in which only the toothed sections are segmented. Segmenting the toothed sections refers to a structure in which only the toothed portions are separate members and can be freely attached to and removed from the circumferential face section of the rollers. Segmenting the toothed portions enables, for example, easily adjusting the mesh depth of the teeth and grooves, changing the draw ratio, and changing the draw pattern. Also, even if the teeth have become worn, they can be easily replaced if spare parts have been prepared, thus enabling shortening downtime and lowering equipment cost. As another configuration, it is possible to employ a sleeve structure. Even with the sleeve structure, it is possible to likewise reduce equipment cost.

Draw processing can be performed on the diaper intermediate body 30 in, for example, the following manner. First, the continuous body of the diaper intermediate body 30 is fed between the pair of toothed rollers 40 and 41. The feeding of the continuous body of the diaper intermediate body 30 between the pair of rollers 40 and 41 is performed while applying constant tension to the continuous body with use of a feeding nip roller (not shown) and a low-speed nip roller (not shown) that are respectively arranged upstream in the direction MD and downstream in the direction MD so as to sandwich the rollers 40 and 41. Between the rollers 40 and 41, a pair of left and right leg opening peripheral edge sections in the diaper intermediate body 30 (central sections in the direction MD of the opposite side edge sections along the direction MD of the diaper intermediate body 30) to which the elastic members 6 have been joined in their stretched state are fed between the high stretch sections 42, the leg opening peripheral edge sections being fed in their stretched state in the stretching direction of the elastic members 6 due to the conveying tension, and the sheets in these fed portions undergo plastic deformation due to the sheet formation components being moderately broken down by stretching and fracture, thus obtaining the draw-processed section P1 that exhibits superior extensibility in the stretching direction of the elastic members 6. On the other hand, in the other sites in the diaper intermediate body 30, the sheets in these sites substantially do not undergo plastic deformation, and therefore there is substantially no improvement in the extensibility.

As described above, in the present embodiment, draw processing is performed on sections in which the elastic members are arranged, with the conjugate sheet (diaper intermediate body 30) stretched in the stretching direction of the elastic members. Here, "with the conjugate sheet stretched in the stretching direction of the elastic members" refers to the state in which, due to the elastic members in the conjugate sheet (the elastic members in the portions subjected to draw processing) being pulled by the conveying tension or the like, the conjugate sheet is stretched to substantially the same stretch rate as the stretch rate at the time when the elastic members were joined and fixed to the sheets configuring the conjugate sheet (hereinafter, also referred to as the "joining-time stretch rate"), and it does not matter whether the sheets configuring the conjugate sheet are stretched. Here, the concept of "a stretch rate substantially the same as the joining-time stretch rate" includes the range from a stretch rate somewhat smaller than the joining-time stretch rate to a stretch rate somewhat larger than the joining-time stretch rate, and specifically, is preferably in the range of 0.5× to 1.5× the joining-time stretch rate.

Next, the continuous body of the diaper intermediate body 30 is fed between the pair of toothed rollers 50 and 51 with use of nip rollers (not shown) similarly to the above description. Between the rollers 50 and 51, the central section, in the CD direction, of part of the hip section E and the waist section D on the back-side section A side in the diaper intermediate body 30 (central section in the direction CD of the MD tip section of the diaper intermediate body 30) to which the elastic members 7 and 8 have been joined in their stretched state is fed between the high stretch sections 52, the central section being fed in its stretched state in the stretching direction of the elastic members 7 and 8, and the sheets in this fed portion undergo plastic deformation due to the sheet formation components being moderately broken down by stretching and fracture, thus obtaining the draw-processed section P2 that exhibits superior extensibility in the stretching direction of the elastic members 7 and 8. On the other hand, in the other sites in the diaper intermediate body 30, the sheets in these sites substantially do not undergo plastic deformation, and therefore there is substantially no improvement in the extensibility.

In this way, after the draw-processed sections P1 and P2 have been formed in the continuous body of the diaper intermediate body 30, the continuous body is cut in units of diaper intermediate bodies, and next, the band-shaped sheet 15 in which the draw-processed section P3 has been formed by separate draw processing is attached to the diaper intermediate body 30 in accordance with a normal procedure, and furthermore members such as the fastening tape pieces 9 and the landing tape pieces 10 are attached, thus obtaining the disposable diaper 1 described above. The draw-processed section P3 in the band-shaped sheet 15 can be formed according to the above-described method of forming the draw-processed sections P1 and P2.

As described above, in the manufacturing method of the present embodiment, the elastic members are first joined to the sheets in their stretched state, and thereafter draw processing is performed on sections in sheets where the elastic members have been joined while keeping the elastic members stretched, thus widening the range of diaper size application and improving the wearing comfort, and furthermore obtaining the draw-processed sections P1 to P3 that also have a pleasing appearance. In contrast, with a method of first subjecting the sheets to draw processing and thereafter joining the elastic members to the draw-processed sections in their stretched state, there is the risk that the high extensibility of the draw-processed sections in the sheets obtained by the draw processing will be impaired by the adhesive used in the subsequent step for joining the elastic members. Also, when the sheets are subjected to draw processing, the sheets are kept stretched and no longer return to their original length on their own, thus making the subsequent joining of the elastic members difficult.

The range of application of the present invention (first invention) is not limited to the expandable-type disposable diaper described above, but rather is suitable for absorbent articles equipped with an absorbent core, such as a pull-on disposable diaper or sanitary napkin, as well as wearing articles not equipped with an absorbent core, examples of which include a medical wearing article such as a surgical gown, or a general wearing article such as a jacket.

For example, in the case of applying the present invention (first invention) to a sanitary napkin, examples of configurations include a configuration in which string-type, band-type, or film-type elastic members are disposed in their stretched state along the edge sections of sheets in the two lengthwise left and right side edge sections of a sanitary napkin, and the elastic member disposition sections in the sheets are subjected to draw processing in the stretching direction of the elastic members. In this configuration, normally, one or more of the elastic members are disposed in the lengthwise central sections of the side edge sections extending along the length direction of the sanitary napkin, similarly to the elastic members 6 in the disposable diaper shown in FIG. 1. The basic configuration of the sanitary napkin is similar to that of the disposable diaper described above, and is provided with a topsheet forming the skin-contacting face, a backsheet forming the skin-non-contacting face, and a liquid-retentive absorbent core disposed between those two sheets. The sanitary napkin may also be equipped with three-dimensional gathers subjected to draw processing, as with the three-dimensional gathers 18 described above.

Although the present invention (first invention) has been described above based on a preferred embodiment, the present invention (first invention) is not limited to the above embodiment. For example, although draw processing is performed on the continuous body of the diaper intermediate body in the above embodiment, draw processing may be performed on one diaper intermediate body that has been manufactured in advance. Also, although draw processing is performed on the diaper intermediate body 30 on which leg periphery cutting (so-called R cutting) has been completed in the embodiment described above, the draw processing may performed before performing R cutting. Also, a configuration is possible in which three-dimensional gathers that have already been subjected to draw processing, or three-dimensional gathers that have not yet been subjected to draw processing, are first attached to the diaper intermediate body 30, and thereafter draw processing is performed at predetermined sites. Furthermore, although the drawing step is carried out in two stages in the embodiment described above, a configuration is possible in which draw processing is carried out on both the leg edge sections (leg periphery) and the waist edge section (hip) in one step. A method of performing draw processing at desired sites in one step simplifies adjustment of the leg periphery and hip manufacturing phase, and also enables reducing the equipment space required and reducing the equipment investment. A method of dividing the drawing step into multiple stages according to the site to be drawn as in the above embodiment facilitates adjustment of the draw ratio. Also, although both the waist edge section arranged around the wearer's waist and the leg edge sections arranged around the wearer's legs are provided in the embodiment described above, the wearing article of the present invention may include only either the waist edge section or the leg edge section.

Also, although a pair of substantially cylindrically toothed rollers are used as the pair of clamps (draw processing devices) having teeth and grooves meshed with each other in the embodiment described above, the draw processing devices are not limited to this, and various types can be used. One example (A) is a draw processing device provided with a pair of conveyor belts (or caterpillars), with elongated projection sections that extend in either the MD or the CD direction being formed continuously. Another example (B) is a draw processing device (also called "stamper" for example) that includes a pair of mutually opposing recession-projection plates, with a multitude of elongated projection sections extending in either the MD or the CD direction being formed on the mutually opposing faces of the pair of recession-projection plates, and that performs draw processing on the object to be draw-processed by using a cam mechanism to change the two recession-projection plates from the state of being separated to the state of being meshed with each other, so as to enable expanding and shrinking the distance therebetween. It is also possible to use the draw processing device disclosed in JP-A-2007-22066 pertaining to a previous application submitted by Applicant.

EXAMPLES

Although the present invention (first invention) is described more specifically below based on Examples, the present invention (first invention) is not to be limited to these Examples.

Example 1

A diaper (medium size, with a total lengthwise length of 440 mm) having a basic configuration similar to that of the expandable-type disposable diaper shown in FIGS. 1 and 2 was manufactured using substantially the same manufacturing method as that in the above-described embodiment. The manufactured diaper was used as a sample of Example 1. In the diaper of Example 1, draw processing was performed on the leg elastic member disposition sections of the leg edge sections and the vicinity thereof, and was not performed on the waist edge section or the three-dimensional gathers. Accordingly, although the draw-processed sections indicated by reference sign P1 in FIG. 1 were formed in the diaper of Example 1, the draw-processed sections indicated by reference signals P2 and P3 were not formed. The draw-processed sections of the diaper of Example 1 spanned from the respective peripheral edges of the pair of left and right leg openings to a position beyond the leg elastic member located most inward in the diaper width direction. The length of each draw-processed section in the diaper length direction was 200 mm, and the length thereof in the diaper width direction was 25 mm. Two leg elastic members were disposed in each of the pair of left and right leg edge sections, and the interval between adjacent leg elastic members was 6 mm. As the constituent members of the diaper, such as the leg elastic members and other types of elastic members and the topsheet and other types of sheets, those used in the commercially available disposable diaper "Merries Airy Mesh" (product name) made by Kao Corporation were used.

Also, in the manufacturing of the diaper of Example 1, steps other than the draw processing were performed according to normal procedures. The draw processing was performed with the leg elastic members being stretched until the total length in the diaper length direction was 440 mm (stretched to a stretch rate substantially the same as the stretch rate at the time of joining the leg elastic members), and the draw ratio resulting from the draw processing was 1.4×. Instead of toothed rollers as shown in FIG. 4, the stamper, as in example (B) above, was used as the draw processing device. The conditions used in the draw processing were as follows. The mesh depth of the teeth and grooves of the draw processing apparatus (depth corresponding to reference sign D in FIG. 5) was 1 mm, the pitch of adjacent teeth (distance corresponding to reference sign P in FIG. 5) was 2 mm, and the tooth width (length in the draw processing direction, corresponding to reference sign W in FIG. 5) was 0.5 mm to 0.7 mm.

Example 2

An expandable-type disposable diaper was manufactured using a method similar to that of Example 1, with the exception of changing the draw ratio resulting from the draw processing to 2.2×. The manufactured diaper was used as a sample of Example 2. In order to set the draw ratio to 2.2×, the mesh depth of the teeth and grooves was changed to 2 mm.

Comparative Example 1

An expandable-type disposable diaper was manufactured using a method similar to that of Example 1, with the exception that draw processing was not performed at all. The manufactured diaper was used as a sample of Comparative Example 1.

Figure 6:
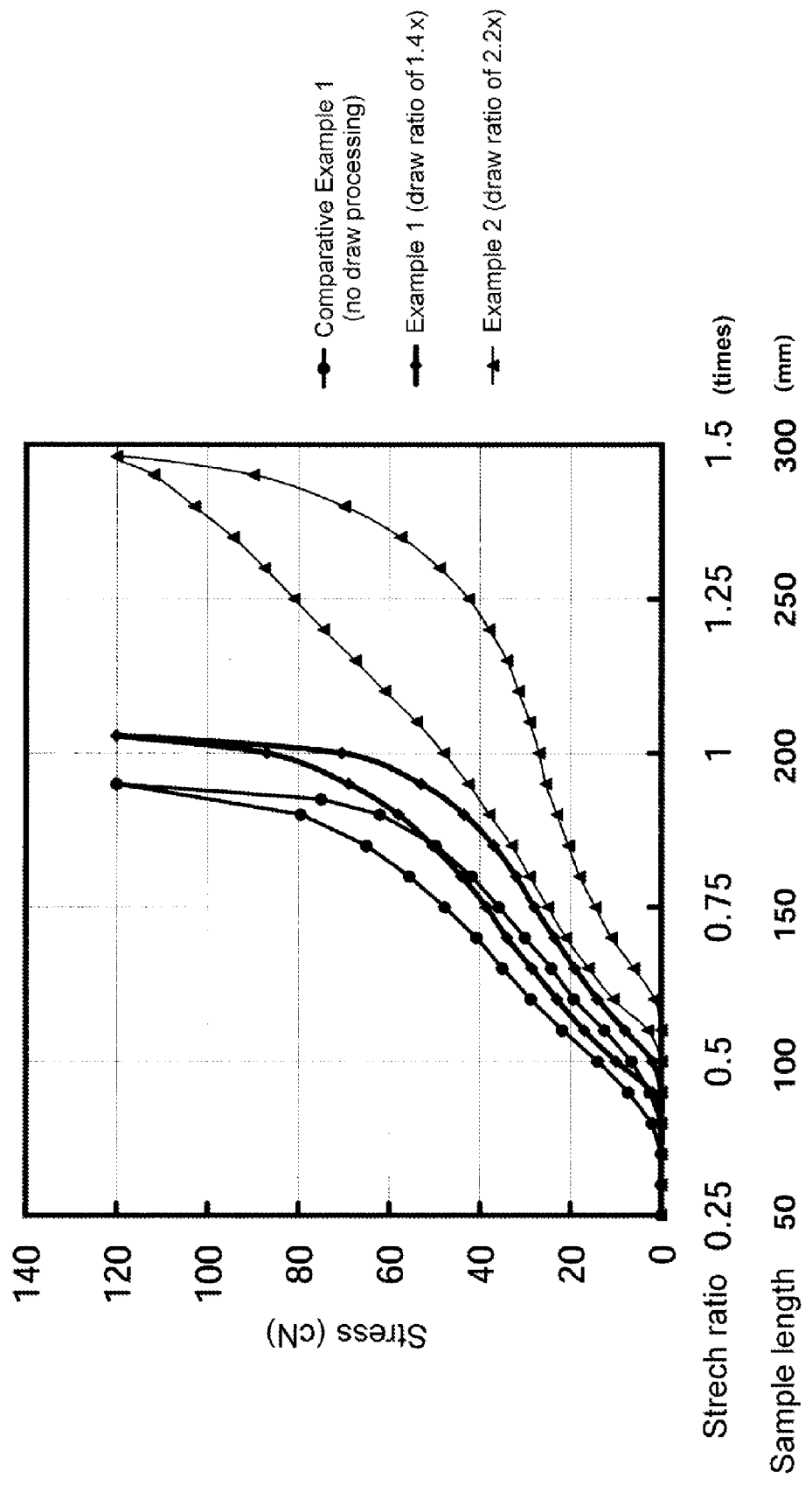
FIG. 6 is a graph showing a stress-to-stretch-ratio curve at the leg edge section in diapers according to Examples according to the present invention (first invention) and a Comparative Example.

The extensibility characteristics of the leg edge sections (portions corresponding to the draw-processed sections in the Examples) in the samples (expandable-type disposable diaper) of the Examples and Comparative Example were evaluated using the following method. A sample was taken by cutting off the leg edge section (a width of 25 mm and a length of 200 mm in the lengthwise central section in one side edge section of the diaper) of the diaper, with the diaper being expanded as shown in FIG. 1 and stretched to the product length (440 mm). The sample was fixed between the chucks (180 mm interval between chucks) of a tensile tester (Tensilon, made by Orientec Co., Ltd.) such that the length direction (stretching direction of the elastic members) conformed to the tensile direction, the sample was pulled by increasing the interval between chucks until the tensile load was 120 cN (outbound trip), and thereafter the interval between chucks was decreased until the tensile load was 0 cN (inbound trip). The stress in the outbound trip and the inbound trip was measured, to create the graph of the stress-to-stretch-ratio curve shown in FIG. 6. In the graph of FIG. 6, the vertical axis indicates stress (cN), the upper legend of the horizontal axis indicates the sample stretch ratio (times) assuming that the reference length of 200 mm is 1×, and the lower legend of the horizontal axis indicates the actual sample length (mm).

As shown in FIG. 6, the slope of the stress-to-stretch-ratio curve of Examples 1 and 2 that were subjected to draw processing is smaller than that of Comparative Example 1 that was not subjected to draw processing. The smaller the slope of the stress-to-stretch-ratio curve, the more readily the leg edge section stretches with a small amount of force. Note that the rising position of stress in Examples 1 and 2 (stretch ratio when the stress has exceeded 0) is shifted toward the right side of the graph relative to Comparative Example 1, but the rising position of stress can be designed freely by adjusting, for example, the draw ratio of the elastic members and the size of the elastic members. Also, a comparison of stretching when the stress is 120 cN shows that, compared to the leg edge section in Comparative Example 1, the leg edge section in Example 1 (draw ratio of 1.4×) is 20 mm longer, and the leg edge section in Example 2 (draw ratio of 2.2×) is 110 mm longer. It is evident from the above description that the leg edge sections of Examples 1 and 2 stretch a greater amount when pulled in the stretching direction of the elastic members, and have high extensibility, that is to say, readily stretch with a small amount of force.

Also, the inbound trip of the stress-to-stretch-ratio curve in FIG. 6 is an indicator of how the leg edge sections come into contact with the wearer's skin while the diaper is worn. When the stress was compared at the same sample length (see the lower legend of the horizontal axis in FIG. 6), it indicates that the smaller the stress, the more softly the leg edge sections come into contact with the wearer's skin, the less constriction, and the less readily edge section marks appear on the skin. A comparison of the Examples and the Comparative Example with respect to the inbound trip shows that when the sample length is 150 mm, the stress of Comparative Example 1 not subjected to draw processing is approximately 35 cN, whereas the stress of Example 1 with a draw ratio of 1.4× is approximately 28 cN, and the stress of Example 2 with a draw ratio of 2.2× is approximately 14 cN. This shows that performing draw processing enables reducing stress and manufacturing edge sections that are gentle on the skin and have superior wearing comfort.

A wearing test was performed with the diaper of Example 2 and the diaper of Comparative Example 1. In the wearing test, the diapers were put on an infant (5 months old), and one panelist was instructed to observe the infant wearing the diaper and make a sensory evaluation. As a result, opinions such as the following were received as advantages of Example 2 over Comparative Example 1: there was ample room around the leg; it was possible to apply the diaper to the infant at a stomach tape mark one mark smaller compared to Comparative Example 1; and the small and regular creases of the gathers were visually pleasing.

The following describes the present invention (second invention) based on preferred embodiments thereof with reference to the drawings. FIGS. 7 to 11 show a pull-on disposable diaper 2A that is a first embodiment of the wearing article of the present invention (second invention). As shown in FIG. 8, the diaper 2A of the first embodiment is a wearing article that has a back-side section A arranged on the back side of the wearer when the diaper is worn, a stomach-side section B arranged on the stomach side, and a crotch section C located therebetween, the back-side section A and the stomach-side section B being configured including sheets (outer-layer sheets 27A and 27B and inner-layer sheets 28A and 28B that configure a later-described exterior body 26), and elastic members 7 and 8 being arranged in the sheets in the back-side section A and the stomach-side section B in their stretched state along the hip direction of the wearer (the width direction of the diaper 2A, which is the Y direction in FIG. 8).

Figure 9:
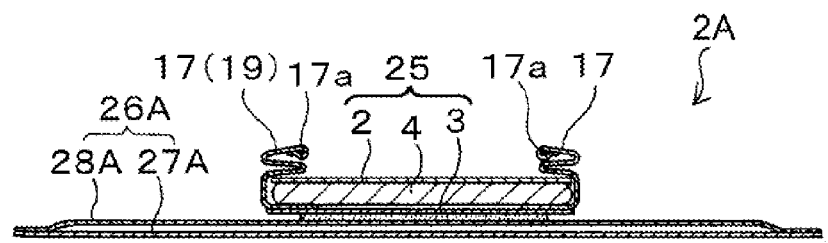
FIG. 9 is a cross-sectional view schematically showing a cross-section taken along line I-I in FIG. 8.

As shown in FIGS. 8 and 9, the diaper 2A includes a substantially elongated (rectangular) absorbent body 25, which includes a liquid-permeable topsheet 2, a liquid-impermeable or liquid-permeation resistant (water repellant or the like) backsheet 3, and a liquid-retentative absorbent core 4 disposed between the two sheets 2 and 3, as well as the exterior body 26 that is located on the skin-non-contacting face side (backsheet 3 side) of the absorbent body 25 and to which the absorbent body 25 is fixed. The absorbent body 25 and the exterior body 26 are joined by an adhesive. The absorbent body 25 is arranged from the back-side section A to the stomach-side section B via the crotch section C. The back-side section A and the stomach-side section B are configured including the absorbent body 25 and the exterior body 26. As shown in FIG. 8, the diaper 2A has an overall hourglass shape in which the lengthwise central section (crotch section C) is narrow.

Note that in the present description, the skin-contacting face is the face of the wearing article and its constituent elements that faces the wearer's skin when the diaper is worn, and the skin-non-contacting face is the face of the wearing article and its constituent elements that faces away from the wearer's skin when the diaper is worn. Also, the length direction is the direction along the long side of the wearing article or the constituent elements of the wearing article, and the width direction is the direction orthogonal to the length direction. In the case of a pull-on wearing article such as the diaper 2A, when the pull-on wearing article is expanded as shown in FIG. 8, the direction along the long side thereof (vertical direction in FIG. 8) is the length direction of the pull-on wearing article, and the horizontal direction in FIG. 8 is the width direction of the pull-on wearing article.

As shown in FIGS. 8 and 9, side cuffs 17 configured by a material that is breathable and liquid-resistant or water-repellant are formed on both the left and right lateral sides of the absorbent body 25. One or more side cuff elastic members 17a are disposed in their stretched state in the vicinity of a free edge section of each side cuff 17. The side cuffs 17 prevent the outflow of liquid by rising up when the diaper is worn. In the first embodiment, an edge section of a sheet member 19 for forming the side cuffs 17, which is on the side opposite from the free edge section, is fixed between the absorbent core 4 and the backsheet 3, but this edge section may be fixed between the backsheet 3 and the exterior body 26.

Figure 10:
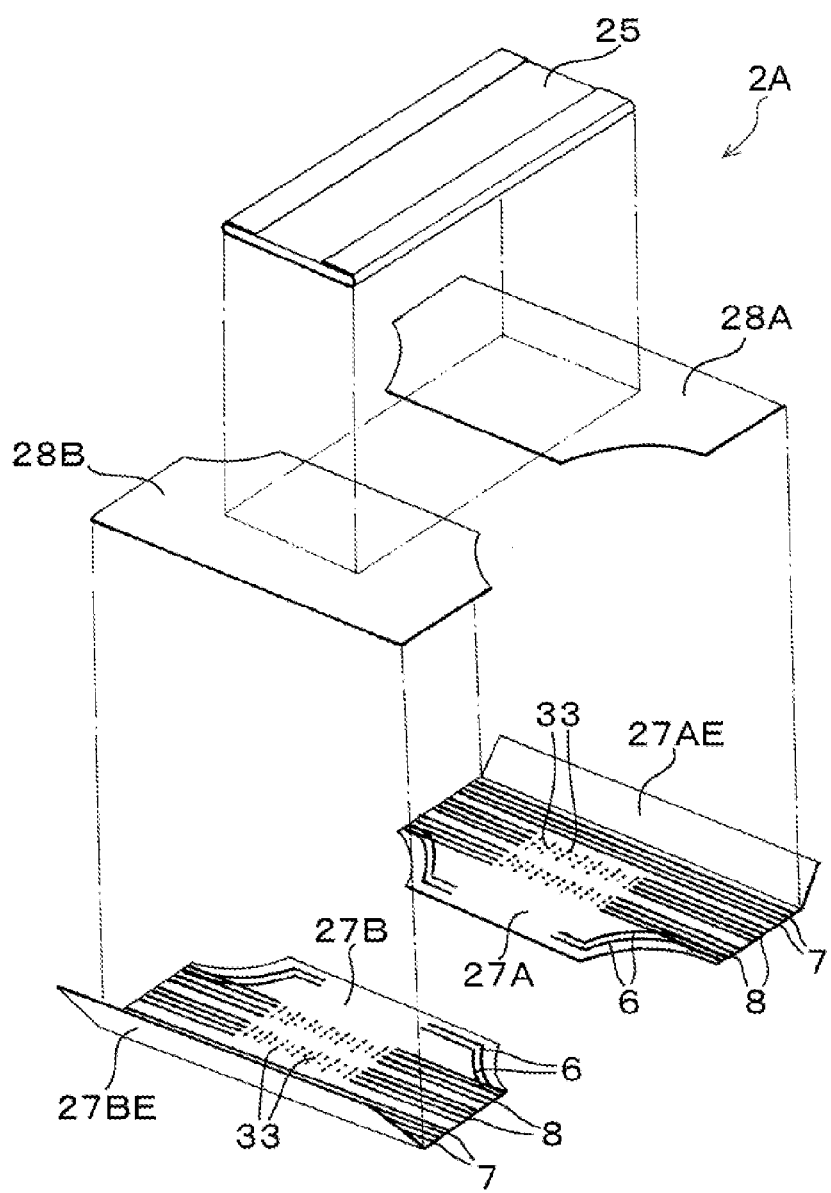
FIG. 10 is an exploded perspective view of the disposable diaper shown in FIG. 7.

As shown in FIGS. 8 and 10, the exterior body 26 is divided into a back-side section A side and a stomach-side section B side. More specifically, the exterior body 26 has a back-side exterior body 26A disposed in the back-side section A and a stomach-side exterior body 26B disposed in the stomach-side section B. The exterior bodies 26A and 26B are disposed with a predetermined interval L2 in the direction orthogonal to the hip direction (i.e., in the length direction of the diaper 2A, which is the X direction in FIG. 8). Furthermore, no exterior body is disposed between the exterior bodies 26A and 26B (the central section in the direction orthogonal to the hip direction of the crotch section C). Although the exterior surface (skin-non-contacting face) of the diaper 2A in the central section of the crotch section C, in which no exterior body is arranged, is formed by the backsheet 3 on the skin-non-contacting face side of the absorbent body 25, an exterior sheet separate from the exterior body 26 may be disposed on the outer side of the backsheet 3. On the other hand, the exterior surface of the diaper 2A in the back-side section A, the stomach-side section B, the portion (back-side crotch section Ca) toward the back-side section A in the crotch section C, and the portion (stomach-side crotch section Cb) toward the stomach-side section B in the crotch section C is formed by the exterior bodies 26A and 26B.

The back-side exterior body 26A has a rectangular shape as seen from above in the back-side section A, and the central section in the diaper width direction in the back-side crotch section Ca protrudes convexly inward in the diaper length direction. The opposite side edges in the diaper length direction in the back-side crotch section Ca of the back-side exterior body 26A are curved into an inward-facing arc, thus forming leg edge sections A3 and A4. The stomach-side exterior body 26B also has a shape similar to that of the back-side exterior body 26A as seen from above, and the opposite side edges in the diaper length direction in the stomach-side crotch section Cb of the stomach-side exterior body 26B are curved into an inward-facing arc, thus forming leg edge sections B3 and B4. In the exterior body 26, the opposite side edge sections A1 and A2 of the back-side exterior body 26A in the back-side section A and the opposite side edge sections B1 and B2 of the stomach-side exterior body 26B in the stomach-side section B are joined together, and this joining forms a pair of side sealing sections S, a waist opening 12, and a pair of leg openings 13 in the diaper 2A. In the side sealing sections S, the stomach-side exterior body 26B and the back-side exterior body 26A are joined by an adhesive, a heat seal, a high-frequency seal, an ultrasonic seal, or the like.

The ratio of the total length L1 of the exterior body 26A or 26B in the direction orthogonal to the hip direction (i.e., in the length direction of the diaper 2A) and the total length L in the same direction of the diaper (the ratio L1/L) is preferably 0.1 to 0.4, or more preferably 0.2 to 0.3. Also, the ratio of the length L2, in the direction orthogonal to the hip direction, of the portion in the crotch section C in which the exterior body 26 is not arranged (i.e., the shortest interval distance between the back-side exterior body 26A and the stomach-side exterior body 26B) and the total length L in the same direction of the diaper (the ratio L2/L) is preferably 0.1 to 0.4, or more preferably 0.2 to 0.3.

As shown in FIG. 10, the back-side exterior body 26A has a structure in which the outer-layer sheet 27A and the inner-layer sheet 28A are laminated. Similarly, the stomach-side exterior body 26B has a structure in which the outer-layer sheet 27B and the inner-layer sheet 28B are laminated. The outer-layer sheets 27A and 27B and the inner-layer sheets 28A and 28B are joined by an adhesive (not shown) at predetermined sites, and in the present embodiment, they are joined over substantially the entire laminated area. In the peripheral edge section of the waist opening 12 (i.e., waist edge section), the outer-layer sheets 27A and 27B have portions 27AE and 27BE that extend beyond the waist edge section side of the inner-layer sheets 28A and 28B when the inner-layer sheets 28A and 28B were laminated (see FIG. 10), and are folded to the absorbent body 25 side. As shown in FIG. 8, the opposite end sections of the absorbent body 25 in the diaper length direction are covered by these folded portions 27AE and 27BE. The folded portions 27AE and 27BE and the portions opposing these portions are joined by an adhesive (not shown) at predetermined sites.

The exterior body 26 (26A and 26B) has extending sections 26E that extend outward in the hip direction from opposite side edges 25s which are along the direction orthogonal to the hip direction in the absorbent body 25 (i.e., the length direction of the diaper 2A). The ratio of the length W1 of the extending section 26E along the hip direction (see FIG. 8) and the length W of the exterior body 26A or 26B along the hip direction (see FIG. 8) (the ratio W1/W) is preferably 0.1 to 0.4, or more preferably 0.15 to 0.3. Note that the lengths W1 and W2 are lengths in the natural state of the completed product (the wearing article that has been subjected to later-described draw processing).

Also, one or a plurality of (in the first embodiment, two) leg elastic members 6 are arranged in the leg edge sections A3 and A4 in the back-side crotch section Ca and the leg edge sections B3 and B4 in the stomach-side crotch section Cb (side edge sections curved in an arc facing inward with respect to the diaper 2A). The leg elastic members 6 located in the back-side crotch section Ca are arranged along the leg edge sections A3 and A4, starting from the vicinity of the back-side crotch section Ca in the opposite side edge sections A1 and A2 of the exterior body 26A, and reaching the side edges 25s of the absorbent body 25. The leg elastic members 6 located in the stomach-side crotch section Cb are arranged along the leg edge sections B3 and B4, starting from the vicinity of the stomach-side crotch section Cb in the opposite side edge sections B1 and B2 of the exterior body 26B, and reaching the side edges 25s of the absorbent body 25. In the expanded state of the diaper shown in FIG. 8, the leg elastic members 6 located on the left side and the leg elastic members 6 located on the right side are arranged bilaterally symmetrically on either side of a virtual straight line (not shown) that laterally bisects the diaper 2A. The leg elastic members 6 are each clamped and fixed in their stretched state between the outer-layer sheets 27A and 27B and the inner-layer sheets 28a and 28B. This forms leg gathers in the back-side crotch section Ca and the stomach-side crotch section Cb. Preferably, at least one elastic member 6 is arranged at a site within 100 mm, or more preferably 0 mm to 50 mm, from opening peripheral edges of the leg openings 13 of the diaper 2A in the worn state.

Waist elastic members 7 are disposed in the waist section D (waist edge section) in the back-side section A and the stomach-side section B, thus forming waist gathers. The waist elastic members 7 are fixed by being clamped in a stretched state between the outer-layer sheets 27A and 27B and the inner-layer sheets 28A and 28B over substantially the entire width along the width direction of the diaper 2A. Preferably, at least one elastic member 7 is arranged at a site within 80 mm, or more preferably 0 mm to 40 mm, from the lengthwise end edge 1a, 1b of the diaper 2A (i.e., the peripheral edge of the waist opening 12). The waist section D is an area that is at a site located around the wearer's waist, and normally has a length that is 1% to 15% of the total lengthwise length L of the diaper 2A (see FIG. 8) from the lengthwise end edge 1a of the diaper 2A in the back-side section A (the lengthwise end edge 1b of the diaper 2A in the stomach-side section B).

Also, a plurality of elastic members 8 for hip gather formation are disposed in the lengthwise opposite side sections of the hip section E (in the vicinity of the waist edge section) in the back-side section A and the stomach-side section B, thus forming a pair of left and right hip gathers. The elastic members 8 for hip gather formation are arranged substantially linearly along the width direction, and are fixed by being clamped in a stretched state between the outer-layer sheets 27A and 27B and the inner-layer sheets 28A and 28B. The hip section E in the back-side section A is an area located below the waist section D and above the crotch section C when, as shown in FIG. 8, the diaper 2A is in a state of being spread out flat (expanded state) by stretching the elastic members of each section, considering the back-side section A side to be the top side and the stomach-side section B side to be the bottom side. The hip section E in the stomach-side section B is an area in substantially the same location as the hip section E in the back-side section A if the diaper 2A is turned upside down from that shown in FIG. 8.

In this way, in the extending sections 26E of the exterior body 26 (26A and 26B) in the back-side section A and the stomach-side section B, a plurality of elastic members 7 and 8 disposed in their stretched state along the hip direction are disposed with a predetermined interval in the direction orthogonal to the hip direction. In the exterior body 26 (extending section 26E) located in the back-side section A or the stomach-side section B, the disposition interval between adjacent elastic members is preferably 2 mm to 20 mm, or more preferably 5 mm to 10 mm. Also, in the exterior body 26 (extending section 26E) located in the back-side section A or the stomach-side section B, the number of elastic members disposed in their stretched state along the hip direction is preferably 3 to 50, or more preferably 5 to 40.

The elastic members 6, 7, and 8 are fixed by being clamped in their stretched state between the outer-layer sheets 27A and 27B and the inner-layer sheets 28A and 28B, with use of an adhesive or the like. In particular, in the later-described draw-processed sections, it is necessary for the elastic members to be fixed between the sheets with use of an adhesive or the like in view of giving the sheets the stretchability (in particular, shrinkability) of the elastic members. Note that although the sheets in the areas where the elastic members are not provided do not need to be joined by an adhesive or the like in the later-described draw-processed sections in view of the above point, it is preferable that the sheets in such areas are joined by an adhesive or the like in view of improving the appearance of the gathers (see FIG. 11).

Although the adhesive for joining the outer-layer sheets and the inner-layer sheets may be used as the adhesive for fixing the elastic members, since the fixing of the elastic members generally requires much more adhesive than the mere joining of sheets, it is preferable that an adhesive for fixing the elastic members is additionally applied separately from the adhesive for joining the outer-layer sheets and the inner-layer sheets from the standpoint of reducing the amount of adhesive used. Although the pattern in which the adhesive for forming the elastic members is applied can be a planar shape, a spiral pattern shape, an omega shape, a summit shape, or the like, in view of the texture and softness of the gathers, it is preferable that the adhesive is directly applied to only the elastic members using a so-called "comb gun" or the like. Note that regarding the later-described draw processing, it is preferable that the elastic members are continuously fixed to the sheets in the range in which the draw processing is performed.

Also, the elastic members 6, 7, and 8 are cut in an area that overlaps with the absorbent body 25 in the back-side section A and the stomach-side section B, thus eliminating their functionality in such areas. The elastic members can be cut with use of known hot embossing processing. If hot embossing processing is used, the hot embossing processing may be performed from the outer-layer sheet 27A and 27B side, or may be performed from the inner-layer sheet 28A and 28B side.

As described above, the absorbent body 25 and the exterior body 26 are joined by an adhesive. The method of joining them may be, other than the application of an adhesive, a method using a means such as heat sealing, ultrasonic sealing, or physical engagement. In particular, the application of an adhesive is preferable due to not causing damage to the constituent materials, and enabling joining of the interface of the joining sections. The shape as seen from above of the adhesive application section can be a conventionally known shape such as a planar shape, a linear shape, a dotted shape, a line-dotted shape, an omega shape, or a spiral shape. The adhesive application device may be contact-type or contactless, and it is possible to use a die coater, a spiral spray, an omega nozzle, a curtain spray, a bead nozzle, a roll coater, a gravure coater, a screen roll coater, or the like. Also, when applying the adhesive, attention should be given in particular to the amount of adhesive used. Application methods that can readily ensure breathability and adhesion strength are preferable, and specific examples include a method of applying an adhesive in stripes with use of any of various types of coaters (a method of disposing a plurality of adhesive application sections extending in a band shape in one direction, with a predetermined interval in the direction orthogonal to that one direction), or a method of applying an adhesive with use of an omega nozzle, a summit nozzle, or the like.

Incidentally, in general, in the joining of the absorbent body and the exterior body, in the case where the exterior body substantially does not have extensibility or stretchability before joining, the form of joining (position, size, and the like of joining sections) can be set arbitrarily without any innovation in particular. However, in the case where the exterior body has extensibility or stretchability during joining—especially in the case of joining the absorbent body in a portion of the exterior body having extensibility or stretchability or the vicinity therefore—it is preferable to make an innovation such as the following. Here, "the case where the exterior body has extensibility or stretchability during joining" includes: (1) the case where at the time of joining of the absorbent body, the exterior body has been given extensibility or stretchability by later-described draw processing; and (2) the case where the exterior body has not been subjected to draw processing at the time of joining the absorbent body, but the exterior body has been given extensibility and stretchability by being provided with elastic members. In the diaper 2A of the first embodiment, at the time of its manufacture, the absorbent body 25 and the exterior body 26 (the continuous body of the exterior body) are joined before draw processing as described later (see FIG. 15), and although the exterior body 26 has not been provided with extensibility or stretchability by draw processing at the time of joining the absorbent body thereto, the exterior body 26 is equipped with the elastic members 6, 7, and 8, and therefore has been given stretchability. Accordingly, in the diaper 2A of the first embodiment, regarding the form of joining the absorbent body 25 and the exterior body 26, it is preferable to make an innovation such as the following.

The innovation regarding the form of joining the absorbent body and the exterior body differs depending the stretch rate of the exterior body when joining the absorbent body and the exterior body. The innovation employed will be described below for: (A) a case where the exterior body is joined to the absorbent body in a state where it is stretched to a low stretch rate that is less than or equal to 1.5× its shrink state (natural state) but can be stretched to, or greater than, its stretched state, and (B) a case where the exterior body is joined to the absorbent body in its stretched state where it has been stretched to a high stretch rate exceeding 1.5× its shrink state.

In the case of example (A), the joining section (adhesive application section) of the absorbent body 25 and the exterior body 26 is preferably located in the central section in the diaper width direction (hip direction Y) in the area in which the absorbent body 25 and the exterior body 26 overlap. The reason for this is as follows. Normally, the absorbent body 25 has the absorbent core 4 that substantially does not have stretchability, and therefore the absorbent body 25 has no stretchability or is very poor in terms of stretchability. On the other hand, the exterior body 26 before joining the absorbent body has the elastic members 6, 7, and 8, and overall has superior stretchability. However, if the surface area of the joining section of the absorbent body 25 with poor stretchability and the exterior body 26 with superior stretchability is too large, the stretchability of the external body 26 is impaired. In particular, when the opposite side edge sections along the diaper length direction of the absorbent body 25 and the vicinity thereof are joined with the exterior body 26, the stretchability of the exterior body 26 may be greatly impaired, and the absorbent body 25 may become detached. Specifically, in the case where the exterior body is joined with the absorbent body when stretched to a low stretch rate, the smaller the surface area of the joining section (surface area of the adhesive application), the exterior body 26 is less prone to be influenced (reduced in stretchability) by being joined with the absorbent body 25 with poor stretchability. Further, by joining the absorbent body 25 and the exterior body 26 in a portion (central section) in the diaper width direction of the absorbent body 25 rather than joining them over the entire width in the diaper width direction of the absorbent body 25, it is possible to more effectively take advantage of the stretchability obtained by the later-described draw processing in the exterior body 26 that extends outward from the joining section (adhesive application section) in the diaper width direction. For the above reason, the joining section of the absorbent body 25 and the exterior body 26 is preferably located in the central section in the diaper width direction in the area in which the absorbent body 25 and the exterior body 26 overlap.

Also, the joining section preferably has a length of approximately 30 mm in the diaper width direction. Configuring the joining section in this way is effective in terms of taking advantage of the stretchability of the exterior body 26 that extends outward from the end section in the diaper width direction of the absorbent body 25, and improving the fit to the wearer.

On the other hand, in the case of (B), the innovation regarding the form of joining the absorbent body 25 and the exterior body 26 is mainly aimed at preventing the absorbent body 25 from becoming detached from the exterior body 26 and making the absorbent body 25 less readily influenced by the shrinking of the exterior body 26. In the diaper 2A obtained employing the case of (B), due to the fact that shrinking force acts not only on the exterior body 26 but also on the absorbent body 25 when the diaper 2A is in its natural state, the absorbent body 25 integrated with the shrunk exterior body 26 also becomes extensible when the diaper is worn. For this reason, the absorbent body 25 readily becomes detached from the exterior body 26; in particular, when the absorbent body 25 is joined to the portion having stretchability (portion provided with the elastic members) in the exterior body 26 and the vicinity thereof, the absorbent body 25 readily becomes detached. One example of an innovation regarding the form of joining in such a case is disabling the stretchability of the portion of the exterior body 26 that has stretchability and that is joined with the absorbent body 25. As a disabling method, it is preferable to perform processing for partially cutting and/or fusing the elastic members disposed in the portion having stretchability in the exterior body 26 before joining the absorbent body thereto, with use of intermittent (partial) pressure application and/or heating. Effects of such disabling processing are disclosed in JP-A-2001-61890. Also, in order to prevent the absorbent body 25 from becoming detached from the exterior body 26 or becoming rolled up when the diaper 2A is worn, the length in the diaper width direction of the joining section (adhesive application section) of the absorbent body 25 and the exterior body 26 is preferably 1/5 to 4/5, or more preferably 2/5 to 4/5, the total width in the diaper width direction of the absorbent body 25.

Note that the above-described innovation regarding the form of joining the absorbent body 25 and the exterior body 26 is to be applied in cases where the absorbent body 25 substantially does not have extensibility or stretchability, as in a normal absorbent body of this type. However, the joining form is not limited to the above in cases where the absorbent body 25 has stretchability (or has an extensible configuration)

As shown in FIG. 8, in the diaper 2A of the first embodiment of the wearing article of the present invention (second invention), the elastic members 6, 7, and 8 are provided in the back-side section A and the stomach-side section B, and the sheets (outer-layer sheets 27A and 27B and the inner-layer sheets 28A and 28B) themselves have been provided with extensibility by draw processing. Here, the concept of "the sheets themselves have been provided with extensibility" includes the case where the sheets themselves that did not originally have extensibility have been given extensibility (by draw processing), as well as the case where the extensibility of the sheets themselves that have extensibility has been further increased (by draw processing). A draw-processed section P4 located in the back-side section A is substantially continuous over the entire length in the direction (length direction X of the diaper 2A) orthogonal to the hip direction of the back-side section A, and a draw-processed section P5 located in the stomach-side section B is substantially continuous over the entire length in the direction orthogonal to the hip direction of the stomach-side section B. Here, the concept "substantially continuous" refers to not only the case where a draw-processed section is continuous without interruption over a predetermined region as in the first embodiment, but also to the case where a plurality of draw-processed sections form a line in a series with a predetermined interval (preferably an interval of 5 mm or less) in the direction orthogonal to the hip direction.

More specifically, the draw-processed section P4 is band-shaped as seen from above (portion with diagonal lines in the back-side section A and the back-side crotch section Ca in FIG. 8), is continuous in the diaper length direction (the direction indicated by reference sign X in FIG. 8) over the entire length of the diaper length direction of the back-side section A and over part of the back-side crotch section Ca, and is formed in the extending section 26E of the back-side exterior body 26A configuring the back-side section A. In the expanded state of the diaper shown in FIG. 8, the draw-processed section P4 located on the left side and the draw-processed section P4 located on the right side are arranged bilaterally symmetrically on either side of a virtual straight line (not shown) that laterally bisects the diaper 2A. Also, the draw-processed section P5 is band-shaped as seen from above (portion with diagonal lines in the stomach-side section B and the stomach-side crotch section Cb in FIG. 8), is continuous in the diaper length direction over the entire length of the diaper length direction of the stomach-side section B and over part of the stomach-side crotch section Cb, and is formed in the extending section 26E of the stomach-side exterior body 26B configuring the stomach-side section B. The draw-processed sections P5 located on the stomach-side section B side are located on extension lines of the draw-processed sections P4 located on the back-side section A side. The draw-processed sections P4 are located inward in the diaper width direction relative to the opposite side edge sections A1 and A2 of the back-side exterior body 26A, and the draw-processed sections P5 are located inward in the diaper width direction relative to the opposite side edge sections B1 and B2 of the stomach-side exterior body 26B.

The sheets in the draw-processed sections P4 and P5 have themselves been provided with extensibility by draw processing, including the elastic member disposition sections in the sheets. In other words, due to the draw processing, in the outer-layer sheets 27A and 27B and the inner-layer sheets 28A and 28B in the draw-processed sections P4 and P5, the sheets undergo plastic deformation due to part or all of the fibers or the like that are formation components of the sheets being stretched and/or fractured and thus broken down, without rupturing. Accordingly, the draw-processed sections readily stretch in the stretching direction of the elastic members and the amount of stretching is increased, compared with sites in the same sheet that have not been subjected to the draw processing (sites that have not been caused to plastically deform). In other words, the sheets themselves in the draw-processed sections P4 and P5 easily and readily stretch in the stretching direction of the elastic members even with low stress. For this reason, compared to the exterior body in a conventional diaper that has not been subjected to draw processing, the draw-processed sections P4 and P5 stretch a greater amount when pulled in the stretching direction of the elastic members, and exhibit high extensibility, that is to say, readily stretch with a small amount of force. Also, in the draw-processed sections P4 and P5, since the elastic members are arranged in their stretched state, even if the sheets that readily stretch in the stretching direction of the elastic members are stretched in the stretching direction, the sheets do not remained stretched out due to the shrinking effect of the elastic members, and therefore shrunk gathers are easily formed as shown in FIG. 11.

Figure 11:
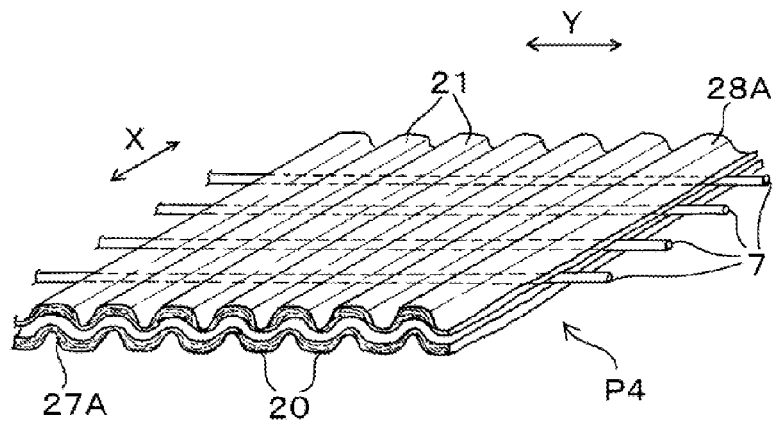
FIG. 11 is a perspective view schematically showing part of a waist edge section that has been subjected to draw processing in the disposable diaper in the expanded state shown in FIG. 8.

FIG. 11 schematically shows part of the draw-processed section P4 of the waist edge section on the back-side section A side in the diaper 2A in the expanded state shown in FIG. 8. As shown in FIG. 11, in the draw-processed section P4, gathers are formed such that a multitude of convex creases 20 and 21 that extend in the direction (length direction of the diaper 2A (direction orthogonal to the hip direction), which is the X direction in FIG. 11) orthogonal to the stretching direction of the elastic members 7 (the width direction of the diaper 2A (hip direction), which is the Y direction in FIG. 11) are aligned along the waist edge sections. In the draw processing performed on the sheets using toothed rollers (a pair of gear rollers whose teeth and grooves are meshed with each in a gear fashion) in the later-described method of manufacturing the diaper 2A, marks of the teeth of the toothed rollers remain on the sheets, thus forming the creases 20 and 21. Gathers are formed as shown in FIG. 11 also in portions of the draw-processed section P4 other than the waist edge sections and in the draw-processed sections P5 on the stomach-side section B side. Details of the draw processing will be described later.

The diaper 2A of the first embodiment has various types of superior effects owing to the draw-processed sections P4 and P5, in which the sheets themselves have been given extensibility in the stretching direction of the elastic members due to the draw processing, being included in the exterior body 26 configuring the back-side section A and the stomach-side section B over the entire length thereof in the direction orthogonal to the hip direction. Specifically, the diaper 2A of the first embodiment has a wider range of size application than that of a non-draw-processed product that has not been subjected to the draw processing and does not have a portion in which the sheets themselves have been given extensibility, and therefore can accommodate various physical features and body types of wearers. Also, the waist edge sections gently come into contact with the wearer's skin, and therefore the diaper 2A has leeway with little constriction, a low likelihood of leaving an impression of edge sections on the skin, and superior wearing comfort. Also, an advantage of the diaper 2A of the present embodiment is that the diaper 2A can be obtained by merely stretching originally provided members without changing the size of the diaper pattern paper (exterior body) or adding new members; therefore, regardless of the fact that the diaper 2A has high performance, a cutback in material fees and a reduction in manufacturing cost can be achieved, and the diaper 2A is environmentally friendly. Also, in the back-side section A and the stomach-side section B of the diaper 2A, by subjecting the sheets constituting these sites to draw processing (a gear drawing method), gathers are formed such that a multitude of creases that extend in the direction orthogonal to the stretching direction of the elastic members are aligned along the edge sections as shown in FIG. 11, and such gathers that have regularly aligned creases improve the exterior (appearance) of the diaper 2A.

In order to ensure appropriate size and ensure the workability of the side sealing sections S, the ratio of the length W2 of the band-shaped draw-processed section P4, P5 along the hip direction to the length W1 of the extending section 26E along the hip direction (the ratio W2/W1) is preferably 0.3 to 0.95, or more preferably 0.5 to 0.9. Note that the draw-processed section P4 on the back-side section A side and the draw-processed section P5 on the stomach-side section B side may have the same length W2, or may have different lengths W2. In the first embodiment, they both have the same length W2.

Although the stretch rate of the draw-processed sections P4 and P5 differs depending on, for example, the stretch ratio of the introduced elastic members, the material of the sheets subjected to draw processing (outer-layer sheets 27 and inner-layer sheets 28), the draw ratio, and the like, the stretch rate is preferably 2% to 500%, or more preferably 50% to 300%.

The stretch rate is measured in the following way. For example, in the case of measuring the stretch rate of the draw-processed section P4, firstly a waist edge section of the diaper 2A is cut off, including the draw-processed section P4 in which the elastic members 7 are arranged in their stretched state. The waist edge section that was cut off is left in a loose state, and a pen or the like is used to make marks on the waist edge section in units of length (50 mm, 100 mm, 200 mm, or the like) in the stretching direction of the elastic members 7. The waist edge section is gripped on both sides outward of the marks, the waist edge section is stretched by being pulled in the stretching direction of the elastic members 7, and the dimension (marginal stretch length) between the marks is measured when the waist edge section can be stretched no farther. The marginal stretch length is divided by the length of the waist edge section before pulling (initial length), 1 is subtracted from the result, and the result of that is multiplied by 100, thus obtaining the stretch rate (%) of the draw-processed section P4. For example, if the initial length of the draw-processed section P4 is 50 mm, and the marginal stretch length is 75 mm, the stretch rate of the draw-processed section P4 is 50%.

The draw-processed sections P4 and P5 are obtained by performing draw processing on predetermined sites (extending sections 26E) of the exterior body 26, which is configured including the sheets and the elastic members joined to the sheets in their stretched state. The elastic members are put in their stretched state in this draw processing. The draw processing performed on sheets such as a nonwoven fabric or a resin sheet is performed using, for example, a gear drawing method of feeding the sheets through a pair of gears having teeth and grooves that are meshed with each other, as will be described later. The gears may be shaped as a pair of gear rollers whose teeth and grooves are meshed in a gear fashion (wavy rollers), or may be shaped as a flat plate. The draw processing can be performed using, for example, the gears disclosed in Patent Literature 1 described above (e.g., see the disclosure of FIGS. 3 and 5 in Patent Literature 1).

In describing the materials for forming the various sections in the diaper 2A, preferably the outer-layer sheets 27 and the inner-layer sheets 28 configuring the exterior body 26 and the topsheet 2 are all sheets subjected to draw processing, and are made up of sheets suited for draw processing. As such a sheet suited for draw processing, it is preferable to use: (1) a sheet that does not have extensibility before drawing processing (i.e., is inextensible) but exhibits stretchability after draw processing; or (2) a sheet somewhat having extensibility (low extensibility) even before draw processing but has improved extensibility after draw processing (gains high extensibility), examples of which include a nonwoven fabric, a resin sheet, an elastomer material, or a sheet conjugate material including an elastomer.

In particular, a nonwoven fabric is preferably used as the topsheet 2, the outer-layer sheets 27, and the inner-layer sheets 28 in view of breathability and extensibility. In particular, a liquid-permeable nonwoven fabric that allows a liquid such as urine to permeate is preferably used as the topsheet 2, and pores are formed as necessary. Also, in particular, a liquid-impermeable, moisture-permeable nonwoven fabric or a water-repellent, moisture-permeable nonwoven fabric is preferably used as the outer-layer sheets 27. Also, a liquid-impermeable resin sheet is preferably used as the inner-layer sheets 28.

Examples of the nonwoven fabric include nonwoven fabrics manufactured by various methods, such as a spun-bonded nonwoven fabric made up of elastic fibers or inelastic fibers, a meltblown nonwoven fabric, an SMS nonwoven fabric in which a spun-bonded nonwoven fabric and a meltblown nonwoven fabric are combined, an air-through nonwoven fabric, a heated roll nonwoven fabric, a spunlace nonwoven fabric, an air-laid nonwoven fabric, and a resin-bond nonwoven fabric. These nonwoven fabrics need to have a certain extent of basis weight and strength in order to prevent rupturing, but on the other hand, preferably the basis weight is 5 $g/m^2$ to 50 $g/m^2$, or more preferably 8 $g/m^2$ to 30 $g/m^2$, in view of the fact that breathability is hindered if the basis weight is too high and the nonwoven fabric is too thick.

Examples of the material of the fibers constituting the nonwoven fabric include synthetic resins such as polyethylene, polypropylene, polyester, or acrylic. The fibers constituting the nonwoven fabric may have been subjected to hydrophilization or water-repellency processing, or may be, for example, a conjugate fiber having a so-called core-in-sheath structure that has a sheath material with thermal adhesiveness at the surface of the core material. Preferably, fibers that readily exhibit extensibility due to draw processing are used in the nonwoven fabric.

Examples of the resin sheet include film-shaped sheets made up of polyethylene, polypropylene, polyester, polyurethane, or the like. The resin sheet may be foamed. In view of softness and strength, the thickness of the resin sheet is preferably 5 µm to 100 µm, or more preferably 8 µm to 30 µm. In view of the same, the basis weight of the resin sheet is preferably 5 $g/m^2$ to 50 $g/m^2$, or more preferably 8 $g/m^2$ to 30 $g/m^2$.

Also, as the absorbent core 4, it is possible to use any product used as an absorbent core in a conventional disposable diaper or sanitary napkin without any particular limitation, and for example, it is possible to use a fiber aggregate made up of hydrophilic fibers such as lumber pulp, or such a fiber aggregate provided with grains of superabsorbent polymer. Such fiber aggregates may be covered by a water permeable sheet such as paper or a nonwoven fabric.

Also, as the various types of elastic members 6, 7, 8, and 17a, it is possible to use a known material conventionally used in this type of diaper, without any particular limitations. Examples of elastic member materials include synthetic rubbers such as styrene-butadiene, butadiene, isoprene, or neoprene, natural rubbers, EVA, SIS (styrene-isoprene-styrene), SEBS (styrene-ethylene-butylene-styrene), SEPS (styrene-ethylene-propylene-styrene), elastic polyolefin, or polyurethane. Also, the form of the various types of elastic members 6, 7, 8, and 17a can be appropriately selected from among thread-like, band-like, ribbon-like, film-like, net-like, and so on, and in particular, a thread-like or ribbon-like elastic member is preferable in view of being low-cost, having superior adhesiveness, having superior stretching responsiveness, and the ease of stress design.

Also, examples of the adhesive used in joining the various types of sheets 27, 28, and 19 to the various types of elastic members 6, 7, 8, and 17a include a styrene-based (SIS, SBS, SEBS) or a polyolefin-based hot-melt adhesive.

Figure 12:
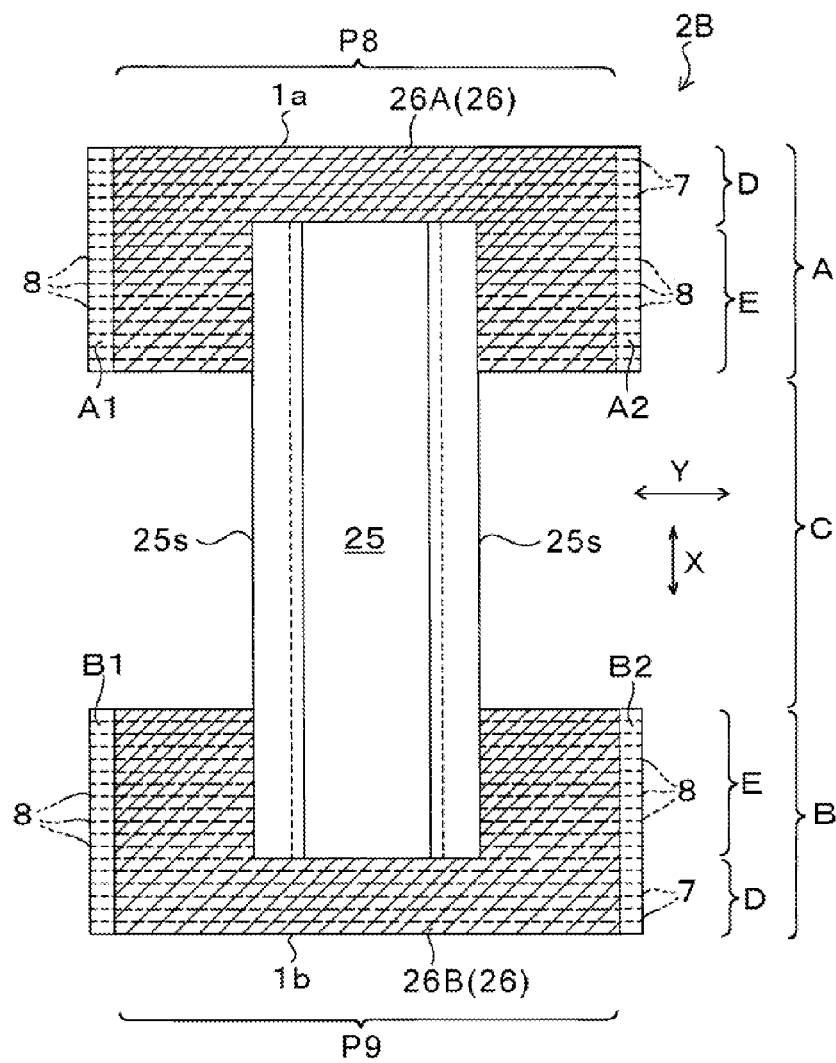
FIG. 12 is a diagram (corresponding to FIG. 8) showing a pull-on disposable diaper according to a second embodiment of the wearing article of the present invention (second invention).
Figure 13:
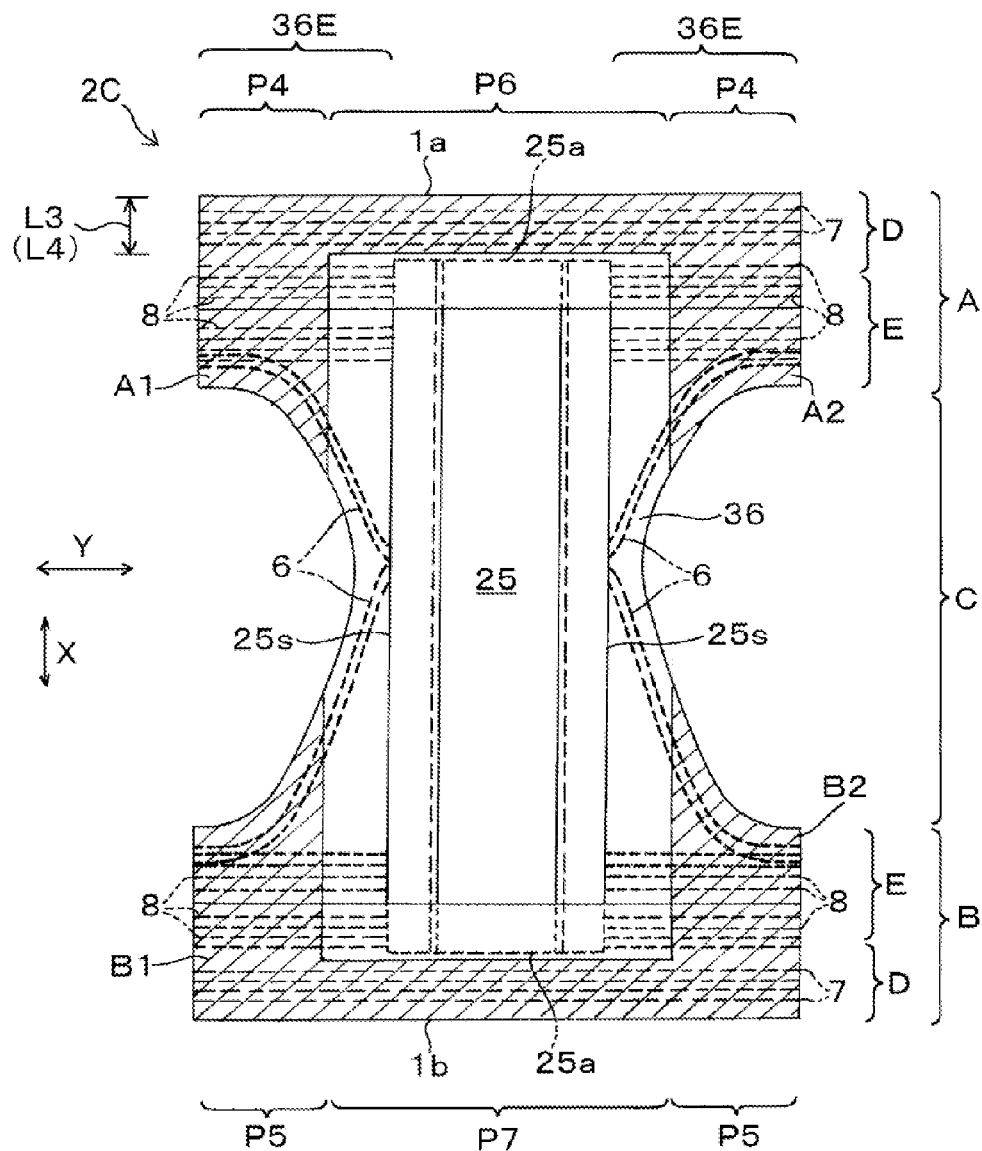
FIG. 13 is a diagram (corresponding to FIG. 8) showing a pull-on disposable diaper according to a third embodiment of the wearing article of the present invention (second invention).
Figure 14:
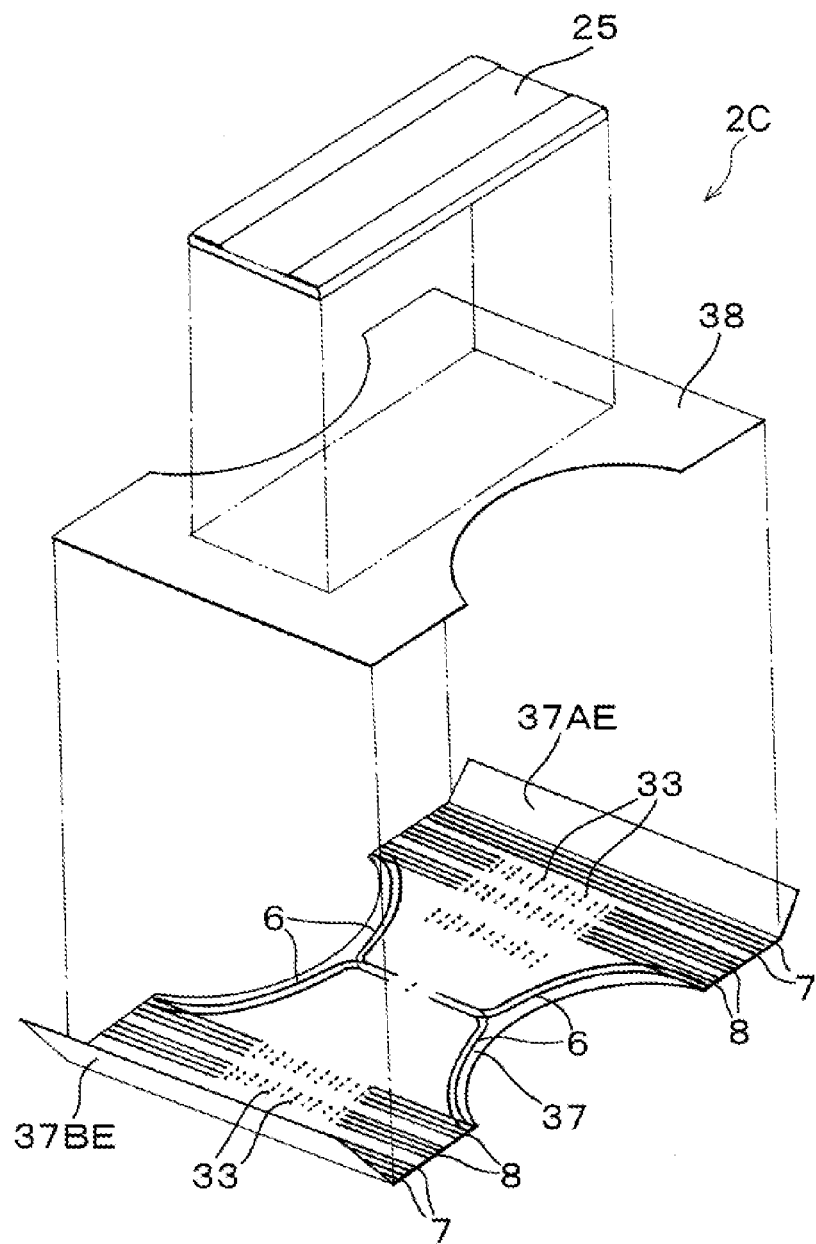
FIG. 14 is an exploded perspective view of the disposable diaper shown in FIG. 13.

Next is a description of another embodiment of the wearing article of the present invention (second invention) with reference to FIGS. 12 to 14. In the following embodiment of the wearing article, constituent portions that differ from the diaper of the first embodiment described above are mainly described, and the same reference signs have been given to constituent portions that are the same, and descriptions thereof have been omitted. Descriptions regarding the diaper of the first embodiment above are to be appropriately applied to constituent portions not particularly described below.

FIG. 12 is a diagram corresponding to FIG. 8 that shows a pull-on disposable diaper of the second embodiment. Whereas the draw-processed sections P4 and P5 in the above-described first embodiment do not overlap with the absorbent body 25, draw-processed sections P8 and P9 in the second embodiment overlap with the absorbent body 25 as shown in FIG. 12. Specifically, in a diaper 2B of the second embodiment, the draw-processed section P8 is formed in substantially the entire area of the back-side exterior body 26A constituting the back-side section A, with the exception of the opposite side edge sections A1 and A2, and the draw-processed section P9 is formed in substantially the entire area of the stomach-side exterior body 26B constituting the stomach-side section B, with the exception of the opposite side edge sections B1 and B2. The sheet draw ratio and stretch rate of the draw-processed sections P8 and P9 can be set similarly to those of the draw-processed sections P4 and P5.

As shown in FIG. 12, the back-side exterior body 26A and the stomach-side exterior body 26B in the second embodiment have rectangular shapes as seen from above, and are disposed with the length direction thereof being in conformity with the width direction Y of the diaper 2B. The plurality of waist elastic members 7 are disposed in the waist section D in the back-side section A and the stomach-side section B, thus forming waist gathers, and a plurality of elastic members 8 for hip gather formation are disposed in the hip section E, thus forming hip gathers. The elastic members 7 and 8 are arranged substantially linearly along the width direction Y over substantially the entire width of the back-side section A and the stomach-side section B, and are fixed by being clamped in their stretched state between two sheets (an inner-layer sheet and an outer-layer sheet) configuring the back-side exterior body 26A and the stomach-side exterior body 26B. The interval between adjacent elastic members 7 and 8 in the length direction X is substantially uniform.

In the first embodiment, the opposite end sections in the length direction X of the absorbent body 25 are covered by folded portions in the sheets (outer-layer sheets) constituting the back-side exterior body 26A and the stomach-side exterior body 26B. However, in the second embodiment, as shown in FIG. 12, the sheets constituting the back-side exterior body 26A and the stomach-side exterior body 26B are not folded, and therefore the opposite end sections in the length direction X of the absorbent body 25 are not covered by the sheets, and the entire area of the skin-contacting face of the absorbent body 25 is exposed.

Since the diaper 2B of the second embodiment has a configuration in which the draw-processed sections P8 and P9 overlap with the absorbent body 25 as described above, in manufacturing the diaper, draw processing is first performed at predetermined sites (substantially the entire area) of the exterior body 26 (continuous body of the exterior body), and thereafter, a step for disposing the absorbent body 25 on the exterior body 26 is carried out. Specifically, in the method of manufacturing the diaper 2B of the second embodiment, the exterior body 26 is given stretchability by the draw processing before the absorbent body 25 is joined. This is a point differing from the later-described method of manufacturing the diaper 2A of the first embodiment (see FIG. 15).

In the method of manufacturing the diaper 2B of the second embodiment, the exterior body 26 (continuous body of the exterior body) has stretchability before the joining of the absorbent body 25, and furthermore the absorbent body 25 is joined to a portion that has stretchability in the exterior body 26, and therefore it is preferable that the above-described innovation is employed regarding the form of joining the absorbent body 25 and the exterior body 26. Specifically, when manufacturing the diaper 2B of the second embodiment, it is preferable to first perform draw processing on the exterior body 26 (the continuous body of the exterior body), thereafter stretch the exterior body 26 in the stretching direction of the elastic members 7 and 8 included in the exterior body 26, and disable the stretchability in the place where the absorbent body 25 is planned to be disposed in the exterior body 26 by, for example, cutting the elastic members in that place, and then dispose and join the absorbent body 25 in the place where it is planned to be disposed. The content described in the first embodiment can be applied to the joining of the absorbent body 25 and the exterior body 26. It is preferable that the joining is performed using an adhesive, and that the adhesive application section has a surface area substantially the same as or smaller than that of the portion where the absorbent body 25 is disposed in the exterior body 26. Effects similar to those of the disposable diaper 2A of the first embodiment can be achieved by the disposable diaper 2B of the second embodiment as well.

Next, a pull-on disposable diaper 2C of a third embodiment of the wearing article of the present invention (second invention) differs from the pull-on disposable diaper 2A of the first embodiment in that an exterior body 36 is configured by two continuous sheets that span from the back-side section A, through the crotch section C, to the stomach-side section B as shown in FIGS. 13 and 14, instead of being divided. In other words, the exterior body 36 of the third embodiment has a structure in which outer-layer sheets 37 and inner-layer sheets 38, which are continuous sheets, are laminated. The sheets 37 and 38 are joined by an adhesive (not shown) at predetermined sites, and in the third embodiment, are joined over substantially the entire laminated area. Also, as shown in FIG. 14, in the peripheral edge section of the waist opening (waist edge section), the outer-layer sheets 37 have portions 37AE and 37BE that extend beyond the waist edge section side of the inner-layer sheets 38 when the inner-layer sheets 38 were laminated, and are folded to the absorbent body 25 side.

The exterior body 36 forms the outer shape of the diaper 2C, and as shown in FIG. 13, opposite edges along the diaper length direction of the crotch section C (the direction orthogonal to the hip direction, which is the X direction in FIG. 13) are curved into an inward-facing arc to form leg edge sections, and overall the exterior body 36 has an hourglass shape in which the central section in the diaper length direction is narrow. The exterior body 36 has extending sections 36E that extend outward in the hip direction from opposite side edges 25s along the direction orthogonal to the hip direction in the absorbent body 25.

Also, as shown in FIG. 13, in the diaper 2C of the third embodiment, two draw-processed sections P4, which are band-shaped as seen from above and are continuous in the diaper length direction over the entire length of the back-side section A in the diaper length direction and span into part of the stomach-side crotch section Cb, are formed in the extending sections 36E located on the left and right sides of the exterior body 36 in the back-side section A; and a draw-processed section P6, which is band-shaped as seen from above and is formed by the same draw processing as that of the draw-processed sections P4, is formed in the exterior body 36 between the pair of left and right draw-processed sections P4 and outward in the diaper length direction relative to the end edge 25a along the hip direction of the absorbent body 25. In the back-side section A, the draw-processed sections P4 and P6 are connected and overall form a squared "U" shape, and the end section on the back-side section A side of the absorbent body 25 is surrounded by the draw-processed sections P4 and P6. In the stomach-side section B as well, draw-processed sections P5 and P7 are formed by performing the same draw processing as that performed on the back-side section A. Likewise to the draw-processed sections P4 and P5, gathers are formed in the draw-processed sections P6 and P7 as well, as shown in FIG. 11. The draw-processed section P6 in the back-side section A and the draw-processed section P7 in the stomach-side section B are located at bilaterally symmetrical positions on either side of a virtual straight line (not shown) that longitudinally bisects the diaper 2C.

The ratio of the length L3 of the draw-processed section P6, P7 in the direction orthogonal to the hip direction to the length L4 of the extending section extending outward from the end edge (lengthwise end edge) 25a along the hip direction of the absorbent body 25 in the exterior body 36 (the ratio L3/L4) is preferably 0.3 to 1, or more preferably 0.5 to 1. Effects similar to those of the disposable diaper 2A of the first embodiment can be achieved by the disposable diaper 2C of the third embodiment as well.

Next is a description of a method of manufacturing the wearing article of the present invention (second invention) with reference to the drawings, taking the example of a method of manufacturing the above-described disposable diaper 2A of the first embodiment. Note that in the later description of the manufacturing method of the present invention (second invention), constituent portions similar to those of the embodiment described above have been given the same reference signs, and descriptions therefore have been omitted. Descriptions in the embodiment described above are to be appropriately applied to constituent portions not particularly described below.

Figure 15:
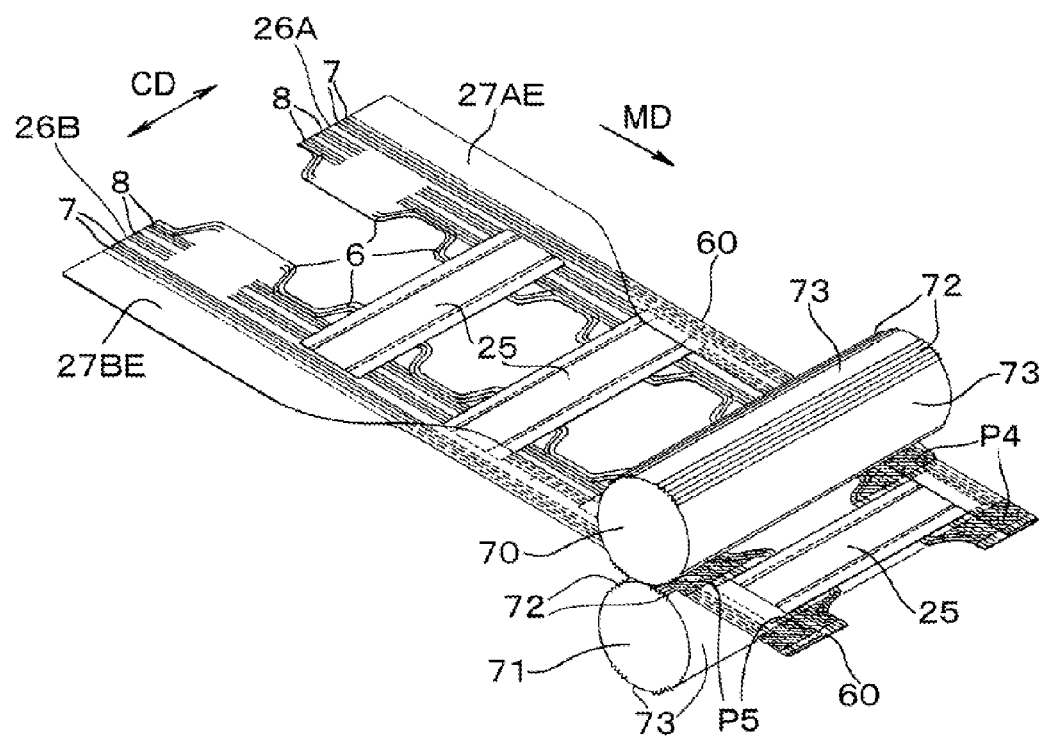
FIG. 15 is a schematic diagram showing a drawing step in the manufacturing of the disposable diaper shown in FIG. 7.

As shown in FIG. 15, the manufacturing method of the diaper of the present embodiment is a so-called "transverse-flow" method of manufacturing a pull-on disposable diaper, and includes: preparing a continuous body of a diaper intermediate body 60 (conjugate sheet) by joining the elastic members 7 and 8, in their stretched state, to sheets (outer-layer sheets 27 and inner-layer sheets 28) configuring the back-side section A and the stomach-side section B of the diaper 2A, the elastic members being joined along the hip direction of the wearer (direction X in FIG. 8); and performing draw processing on predetermined sections of the back-side section A and the stomach-side section B in the diaper intermediate body 60 by feeding the predetermined sections between a pair of toothed rollers (clamp bodies) 70 and 71 that have teeth and grooves meshed with each other, the predetermined sections being fed with the diaper intermediate body 60 stretched in the stretching direction of the elastic members 7 and 8.

More specifically, the diaper manufacturing method of the present embodiment has: (1) a step of forming a continuous body of the exterior body 26 (26A and 26B); (2) an absorbent body disposition step of disposing the absorbent body 25 on the continuous body of the exterior body 26 (a step of forming a continuous body of the diaper intermediate body); and (3) a step of performing draw processing on predetermined sections of the continuous body of the exterior body 26. In other words, the draw processing in the diaper manufacturing method of the present embodiment is carried out after the disposition of the absorbent body.

In the step of forming the continuous body of the exterior body 26 (not shown), firstly the continuous body of the band-shaped exterior body 26A is formed by joining the band-shaped outer-layer sheet 27A and inner-layer sheet 28A, and the continuous body of the band-shaped exterior body 26B is formed by joining the band-shaped outer-layer sheet 27B and inner-layer sheet 28B. In the present embodiment, when these sheets are joined together, the elastic members 6, 7, and 8 are supplied between the sheets, and are joined at predetermined sites between the sheets in their stretched state. Specifically, before overlaying the sheets 27 and 28, an adhesive for fixing the sheets 27 and 28 and the elastic members 6, 7, and 8 is applied to predetermined sites on either of the sheets or mutually opposing faces of both of the sheets, the adhesive is applied to the elastic members 6, 7, and 8 as well, and the sheets 27 and 28 are clamped and pressed by nip rollers, with the elastic members sandwiched therebetween in their stretched state. Also, the sheets 27 and 28 are joined to each other at predetermined sites by a joining means such as an adhesive or various types of sealing such as heat sealing.

Next, the continuous bodies of the thus-formed band-shaped exterior bodies 26A and 26B are conveyed in the same direction lined up parallel to each other, and then respectively cut at predetermined sites (inward of a curve disposition portion of the elastic members 6), thus forming leg edge sections (side edge sections curved in an arc facing inward with respect to the diaper 2A). FIG. 15 shows the continuous bodies of the exterior bodies 26A and 26B after the leg edge sections have been formed. The cutting of the exterior bodies for forming the leg edge sections can be performed using a rotary cutter, a laser cutter, or the like. Note that the leg edge sections can be formed after the below-described disposition of the absorbent body 25.

In the step of disposing the absorbent body 25, absorbent bodies 25, which are manufactured separately and have an adhesive such as a hot-melt adhesive applied thereon in advance, are supplied and fixed onto the inner-layer sheets 28A and 28B so as to span the exterior body 26A and the exterior body 26B that are lined up in parallel with a predetermined interval therebetween. The absorbent bodies 25 can be manufactured according to a manufacturing method normally used in this technical field. After the disposition of the absorbent bodies 25, the extending sections 27AE and 27BE extending outward from the inner-layer sheets 28 in the outer-layer sheets 27A and 27B are folded onto the absorbent bodies 25 and fixed with an adhesive. In this way, the continuous body of the diaper intermediate body 60 is obtained.

In the present embodiment, draw processing is performed using the pair of toothed rollers 70 and 71 on predetermined sites of the continuous body of the thus-obtained diaper intermediate body 60. The paired toothed rollers 70 and 71 have teeth and grooves that extend in the roller axis direction (CD) on the circumferential face sections thereof, and that are meshed with each other. More specifically, as shown in FIG. 15, a pair of high stretch sections 72 provided with teeth and grooves formed thereon that extend in the roller axis direction is formed separated from each other in the roller circumference direction on the circumferential face section of each of the paired toothed rollers 70 and 71, and a substantially flat low or non-stretching section 73 not provided with teeth and grooves is formed between the adjacent pairs of high stretch sections 72 on each roller. The high stretch sections 72 have a substantially rectangular shape and are formed spanning the entire length in the axis direction of the rollers, such that the length direction of these sections conforms with the roller axis direction. The pairs of high stretch sections 72 on the rollers 70 and 71 are formed so as to periodically mesh with each other as the rollers rotate.

Figure 16:
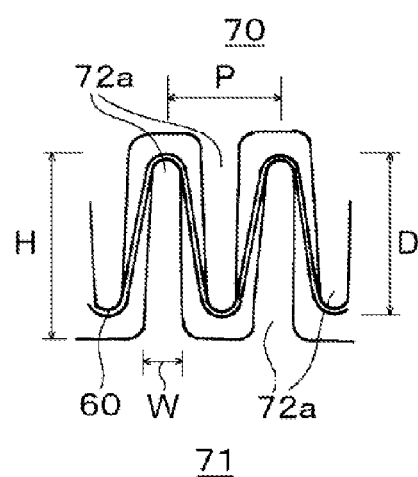
FIG. 16 is a schematic diagram showing how draw processing is performed on a conjugate sheet (diaper intermediate body) by toothed rollers in the drawing step shown in FIG. 15.

As shown in FIG. 16, teeth 72a having a predetermined height H are formed in each high stretch section 72, and when the high stretch sections 72 of the pairs of toothed rollers 70 and 71 mesh with each other, the teeth and grooves of the rollers mesh with each other to a predetermined mesh depth D. For this reason, in the object to be draw-processed (the diaper intermediate body 60), in the sheets in sections that have been fed between mutually opposing high stretch sections 72, part or all of the fibers that are the formation components of the sheets are stretched and broken, and the sheets plastically deform by being broken down to the extent that, as a whole, they do not rupture, thus obtaining high stretch areas that exhibit superior extensibility in the conveying direction (MD) of the object to be draw-processed.

The end faces of the teeth 72a extending in the roller axis direction (CD) have a smooth surface shape in order to do as little localized damage as possible to sheet material and the elastic members during draw processing. Due to the teeth 72a having such a shape, when the object to be draw-processed is fed, it is possible to reduce the amount of damage done to the object to be draw-processed. Also, it is possible to further reduce the damage done to the material by subjecting the object to be draw-processed to the draw processing in gradation through, for example, gradually changing the height of the teeth of the high stretch sections 72 from the opposite end edges in the roller axis direction toward the central section. Gradation refers to gradually changing the draw ratio by, for example, giving the teeth a tapered shape as described above, in order to create a smooth boundary between the portions subjected to draw processing and the portions not subjected to draw processing, and thus reducing the change in the draw ratio between a draw-processed section at which the draw ratio exceeds 1× and a portion that was not subjected to draw processing (section with a draw ratio of 1×).

On the other hand, the low or non-stretching sections 73 of the pair of toothed rollers 70 and 71 do not have teeth and grooves formed thereon and are substantially flat as described above, and therefore, in the object to be draw-processed (the diaper intermediate body 60), the sheets in the portion that has passed through the mutually opposing low or non-stretching sections 73 substantially do not undergo plastic deformation, and become low or non-stretched areas that substantially do not exhibit extensibility.

In order to raise the draw ratio of the object to be draw-processed and give the object to be draw-processed favorable extensibility, the mesh depth D (see FIG. 16) between the high stretch sections 72 of the pair of toothed rollers 70 and 71 is, although depending on the material of the object to be draw-processed, preferably 0.5 mm or more, or more preferably 0.5 mm to 5 mm. As shown in FIG. 16, the mesh depth D of the pair of toothed rollers 70 and 71 is the length for which adjacent teeth 72a overlap each other when the toothed rollers 70 and 71 are meshed together and rotated.

In the present embodiment, from the viewpoint of reliably achieving effects obtained by the above-described draw-processed sections P4 and P5, the draw ratio (draw ratio of the sheets in the draw-processed sections) achieved by the draw processing performed on the object to be draw-processed (diaper intermediate body 60) is preferably 1.02× or more, or more preferably 1.1× or more. In other words, the draw ratio (stretch ratio) of the sheets and elastic members in the portions where the high stretch sections 72 mesh with each other is preferably 1.02× or more, or more preferably 1.1× or more. Specifically, if the draw ratio is too high, there is the risk of leading to, for example, insufficient sheet strength due to the draw processing causing too much damage to the sheets, and therefore the maximum draw ratio is, although depending on the material used for the sheets, preferably approximately 5.0×. Here, the draw ratio indicates how-many-fold the original sheets are to be drawn according to the settings of the draw processing devices such as rollers having teeth and grooves, and therefore is defined as "material length after material has been drawn by meshing of rollers having teeth and grooves"/ "material length before performing drawing by meshing of rollers". The draw ratio can be adjusted through the mesh depth of the teeth in the draw processing apparatus having teeth and grooves, the pitch of adjacent teeth, the width of the teeth, and the like.

Also, the pitch P of adjacent teeth (see FIG. 16) of the high stretch sections 72 of the toothed rollers 70 and 71 is preferably 0.5 mm to 20 mm, or more preferably 0.5 mm to 10 mm. Also, the width of the teeth 72a W (largest width, see FIG. 16) is preferably less than ½ the pitch P, and furthermore the height H of the teeth 72a (see FIG. 16) is preferably 0.5 mm to 20 mm, or more preferably 0.5 mm to 10 mm. If the form of the teeth and grooves of the toothed rollers 70 and 71 satisfy such conditions, the object to be draw-processed (diaper intermediate body 60) that is fed between the toothed rollers 70 and 71 can be given high extensibility.

Note that the pitch of the teeth refers to the distance between the center line of one tooth and the center line of an adjacent tooth. The width of the teeth of the toothed rollers refers to the width of one tooth. The width W of the teeth 72a may be uniform across the tooth height direction, may be trapezoidal so as to decrease from the base of a tooth toward the tip, or may be rectangular, triangular, or the like. The height of the teeth of the rollers refers to the height from the base of a tooth to the tip.

In general, a gear defined in JIS B1701 is attached to the roller shafts of the toothed rollers 70 and 71 as a drive gear, separately from the teeth 72a. Then, by rotating due to the meshing of these drive gears, the rollers 70 and 71 rotate in synchronization without direct contact between the teeth 72a of the rollers 70 and 71.

The interval between the toothed rollers 70 and 71 through which the object to be draw-processed passes, can be appropriately set finely, and controlling the intervals enables easily changing the draw ratio of the object to be draw-processed. One of the toothed rollers in the pair is provided with an elevating device with use of a cylinder or the like (not shown), thus easily controlling the interval. Although not shown, a shim or the like can be used to finely adjust the intervals. Note that although the toothed rollers are configured such that the toothed sections and rollers are made integrally as a single unit in the illustrated example, a configuration is possible in which only the toothed portions are segmented. Segmenting the toothed sections refers to a structure in which only the toothed sections are separate members and can be freely attached to and removed from the circumferential face section of the rollers. Segmenting the toothed portions enables, for example, easily adjusting the mesh depth of the teeth and grooves, changing the draw ratio, and changing the draw pattern. Also, even if the teeth have become worn, they can be easily replaced if spare parts have been prepared.

Draw processing can be performed on the diaper intermediate body 60 in, for example, the following manner. First, the continuous body of the diaper intermediate body 60 is fed between the pair of toothed rollers 70 and 71. The feeding of the continuous body of the diaper intermediate body 60 between the pair of rollers 70 and 71 is performed while applying constant tension to the continuous body with use of a feeding nip roller (not shown) and a low-speed nip roller (not shown) respectively arranged upstream in the direction MD and downstream in the direction MD so as to sandwich the rollers 70 and 71. Between the rollers 70 and 71, in the diaper intermediate body 60, the pair of left and right extending sections 26E of the exterior bodies 26A and 26B are fed between the high stretch sections 72 in its stretched state in the stretching direction of the elastic members 7 and 8, over the entire length in the direction CD of the exterior bodies 26A and 26B, and the sheet formation components in these fed portions undergo plastic deformation due to being moderately broken down, thus obtaining the draw-processed sections P4 and P5 that exhibit superior extensibility in the stretching direction of the elastic members 7 and 8. On the other hand, in the remaining sites in the diaper intermediate body 60, the sheets in these sites substantially do not undergo plastic deformation, and therefore there is substantially no improvement in the extensibility.

As described above, in the present embodiment, draw processing is performed on sections in which the elastic members have been arranged, with the conjugate sheet (diaper intermediate body 60) stretched in the stretching direction of the elastic members. Here, "with the conjugate sheet stretched in the stretching direction of the elastic members" refers to the state in which, due to the elastic members in the conjugate sheet (the elastic members in the portions subjected to draw processing) being pulled by the conveying tension or the like, the conjugate sheet is stretched to substantially the same stretch rate as the stretch rate at the time when the elastic members were joined and fixed to the sheets configuring the conjugate sheet (hereinafter, also referred to as the "joining-time stretch rate"), and it does not matter whether the sheets configuring the conjugate sheet are stretched. Here, the concept of "a stretch rate substantially the same as the joining-time stretch rate" includes the range from a stretch rate somewhat smaller than the joining-time stretch rate to a stretch rate somewhat larger than the joining-time stretch rate, and specifically, is preferably in the range of 0.5× to 1.5× the joining-time stretch rate.

After forming the draw-processed sections P4 and P5 in the continuous body of the diaper intermediate body 60 in this way, a normal procedure is used to fold each absorbent body 25 in two, then form side sealing sections S (not shown in FIG. 15) by performing heat sealing at predetermined intervals in the direction MD on the continuous body using a sealing device (not shown), and then cutting the continuous body at the side sealing sections S using a cutting means (not shown) to obtain individually separated diapers 2A.

As described above, in the manufacturing method of the present embodiment, the elastic members are first joined to the sheets in their stretched state, and thereafter draw processing is performed on sections of the sheets where the elastic members have been joined while keeping the elastic members stretched, thus widening the range of diaper size application and improving the wearing comfort, and furthermore obtaining the draw-processed sections P4 to P5 that also have a pleasing appearance. In contrast, with a method of first subjecting the sheets to draw processing and thereafter joining the elastic members to the draw-processed sections in their stretched state, there is the risk that the high extensibility of the draw-processed sections in the sheets obtained by the draw processing will be impaired by the adhesive used in the subsequent step for joining the elastic members. Also, when the sheets are subjected to draw processing, the sheets are kept stretched and no longer return to their original length on their own, thus making the subsequent joining of the elastic members difficult.

The range of application of the present invention (second invention) is not limited to the expandable-type disposable diaper described above, but rather is suitable for absorbent articles equipped with an absorbent core, such as a pull-on disposable diaper or sanitary napkin, as well as wearing articles not equipped with an absorbent core, examples of which include a medical wearing article such as a surgical gown, or a general wearing article such as a jacket.

Although the present invention (second invention) has been described above based on a preferred embodiment, the present invention (second invention) is not limited to the above embodiment. For example, although the draw-processed section exists in both the back-side section A and the stomach-side section B in the first and second embodiments, the draw-processed section may exist in only either the back-side section A or the stomach-side section B. Also, although the draw-processed section also exists in portions (back-side crotch section Ca and stomach-side crotch section Cb) other than the back-side section A and the stomach-side section B in the first and second embodiments, the draw-processed section may exist in only the back-side section A and/or the stomach-side section B. Also, in the first embodiment, the exterior bodies 26A and 26B may each have a rectangular shape as seen from above.

Also, although the draw-processed sections P4 or P5 are formed one each on both the left and right sides of the absorbent body 25 in the back-side section A or the stomach-side section B respectively in the first embodiment as shown in FIG. 8, a configuration is possible in which a plurality of the draw-processed sections P4 or P5 are formed on both the left and right sides of the absorbent body 25 in the back-side section A or the stomach-side section B. In this case, the plurality of draw-processed sections P4 (P5) can be disposed with a predetermined interval in the hip direction (the width direction of the diaper 2A, which is the Y direction in FIG. 8).

Also, although the above embodiment (the diaper manufacturing method of the first embodiment) is a so-called "transverse-flow" method, in which a continuous body formed by diaper intermediate bodies being connected in the width direction is handled, a so-called "longitudinal-flow" method may be used, in which a continuous body formed by diaper intermediate bodies being connected in the length direction is handled. Also, although the drawing step is performed on the exterior body 26 after the absorbent body 25 has been disposed on the exterior body 26 in the above embodiment, the exterior body 26 may be subjected to draw processing before disposition of the absorbent body 25, and this is preferable in particularly the diaper manufacturing method of the second embodiment. Also, in the above embodiment, a configuration is possible in which draw processing is performed on one of opposite sides of the diaper intermediate body sandwiching the absorbent body 25 disposition area, then the absorbent body 25 is disposed, and thereafter draw processing is performed on the other side. Also, in the above embodiment, a configuration is possible in which, in the case of disposing the absorbent body 25 on the exterior body 26 after performing draw processing on the exterior body 26, the outer-layer sheets 27A and 27B are configured without the portions 27AE and 27BE folded onto the absorbent body 25 (see the second embodiment), or draw processing is performed on the area of the folded portions 27AE and 27BE after the absorbent body 25 has been disposed.

Also, although draw processing is performed on the continuous body of the diaper intermediate body in the above embodiment, draw processing may be performed on one diaper intermediate body that has been manufactured in advance. Also, although draw processing is performed on the diaper intermediate body 60 on which cutting (so-called R cutting) for forming the leg edge sections has been completed in the embodiment described above, the draw processing may performed before performing R cutting.

The invention claimed is:

1. A wearing article, comprising:
a plurality of sheets;
wherein at least one sheet of the plurality of sheets comprises a section in which an elastic member has been disposed, in its stretched state, on the sheet, wherein a disposition section of the sheet where the elastic member has been disposed is provided with extensibility by subjecting the disposition section to draw processing in a stretching direction of the elastic member;
wherein the elastic member is joined to the sheet in its stretched state and thereafter draw processing is performed on the disposition section of the sheet while keeping the elastic member stretched;
wherein gathers are formed in the draw-processed disposition section such that a multitude of creases of the elastic member are regularly aligned;
wherein in the disposition section of the sheet, a plurality of thread-like elastic members are disposed between the plurality of the sheets with a predetermined interval;
wherein the creases of one sheet and the creases of another sheet form an undulating line along the stretching direction of the elastic member; and
wherein the elastic members are continuously fixed to the sheets in the range in which the draw processing is performed.

2. The wearing article according to claim 1, wherein:
the wearing article has an edge section configured including the sheet;
on the sheet in the edge section, the elastic member is disposed in its stretched state along the edge section; and
the disposition section of the sheet where the elastic member has been disposed is subjected to draw processing in the stretching direction of the elastic member.

3. The wearing article according to claim 2, comprising, as said edge section, a waist edge section to be arranged around a wearer's waist or a leg edge section to be arranged around the wearer's leg.

4. The wearing article according to claim 3, wherein:
the wearing article is provided with a three-dimensional gather, one edge section side of the three-dimensional gather being fixed on a face of the sheet forming the wearing article and the other edge section side thereof being able to rise above said face with the fixed end serving as a rising base end, the three-dimensional gather including a band-shaped sheet and an elastic member arranged, in its stretched state, on the other edge section side of the band-shaped sheet or a vicinity thereof; and
a disposition section of the band-shaped sheet where the elastic member has been disposed is subjected to draw processing in the stretching direction of the elastic member.

5. The wearing article according to claim 1, wherein:
the wearing article has a back-side section to be arranged on a back side of a wearer and a stomach-side section to be arranged on a stomach side of the wearer, the back-side section and the stomach-side section each being configured including the sheet;

on the sheet in the back-side section and/or the stomach-side section, the elastic member is disposed in its stretched state along a hip direction of the wearer; and a draw-processed section is formed in the back-side section and/or the stomach-side section, the draw-processed section including the elastic member and being made by providing the sheet itself with extensibility by draw processing.

6. The wearing article according to claim 5, wherein the draw-processed section is continuously spanning the entire length in a direction orthogonal to the hip direction of the back-side section or the stomach-side section, and optionally a plurality of draw-processed sections form a line in a series with a predetermined interval of 5 mm or less in the direction orthogonal to the hip direction.

7. The wearing article according to claim 5, wherein a draw ratio of the sheet in the draw-processed section is at least 1.02 times.

8. The wearing article according to claim 5, wherein a pair of side sealing sections, a waist opening, and a pair of leg openings are formed by joining opposite side edge sections of the sheet in the back-side section with opposite side edge sections of the sheet in the stomach-side section.

9. The wearing article according to claim 5, comprising an absorbent body including an absorbent core and an exterior body that is located on a skin-non-contacting face side of the absorbent body and to which the absorbent body is fixed, wherein the back-side section and the stomach-side section are configured including the exterior body.

10. The wearing article according to claim 9, wherein:
the exterior body has extending sections that extend outward in the hip direction from respective edges of the absorbent body located along a direction orthogonal to the hip direction; and
the draw-processed section exists in the extending sections.

11. The wearing article according to claim 9, wherein the exterior body has a back-side exterior body disposed in the back-side section and a stomach-side exterior body disposed in the stomach-side section, the back-side and stomach-side exterior bodies being disposed with a predetermined interval in the direction orthogonal to the hip direction, and the exterior body not being disposed between the back-side and stomach-side exterior bodies.

12. A method of manufacturing the wearing article according to claim 2, comprising:
preparing a conjugate sheet by joining an elastic member, in its stretched state, to an edge section of a sheet along the edge section; and
performing draw processing on a section of the conjugate sheet where the elastic member has been disposed by feeding the section between a pair of clamp bodies having teeth and grooves meshed with each other, the section being fed with the conjugate sheet stretched in a stretching direction of the elastic member.

13. A method of manufacturing the wearing article according to claim 5, comprising:
preparing a conjugate sheet by joining an elastic member, in its stretched state, to a sheet configuring a back-side section or a stomach-side section of the wearing article, the elastic member being joined along a hip direction of a wearer; and
performing draw processing on a predetermined section of the back-side section or the stomach-side section in the conjugate sheet by feeding the predetermined section between a pair of clamp bodies having teeth and grooves meshed with each other, the predetermined section being fed with the conjugate sheet stretched in a stretching direction of the elastic member.

14. The method of manufacturing a wearing article according to claim 12, wherein a draw ratio achieved by the draw processing is at least 1.02 times.

* * * * *